United States Patent
Sørensen

(10) Patent No.: US 11,938,662 B2
(45) Date of Patent: Mar. 26, 2024

(54) TIP PART ASSEMBLY FOR AN ENDOSCOPE

(71) Applicant: Ambu A/S, Ballerup (DK)

(72) Inventor: Morten Sørensen, Ballerup (DK)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 17/013,463

(22) Filed: Sep. 4, 2020

(65) Prior Publication Data

US 2021/0068641 A1 Mar. 11, 2021

(30) Foreign Application Priority Data

Sep. 6, 2019 (EP) ...................................... 19195989
Sep. 6, 2019 (EP) ...................................... 19195995

(Continued)

(51) Int. Cl.
*B29C 45/14* (2006.01)
*A61B 1/00* (2006.01)
(Continued)

(52) U.S. Cl.
CPC .... *B29C 45/14467* (2013.01); *A61B 1/00094* (2013.01); *A61B 1/00105* (2013.01);
(Continued)

(58) Field of Classification Search
CPC . A61B 1/051; A61B 1/00094; A61B 1/00105; A61B 1/0011; A61B 1/00124;
(Continued)

(56) References Cited

U.S. PATENT DOCUMENTS 4,779,130 A 10/1988 Yabe
5,609,561 A 3/1997 Uehara et al.
(Continued)

FOREIGN PATENT DOCUMENTS

CN 201499375 U 6/2010
CN 104995907 A * 10/2015 ......... A61B 1/00018
(Continued)

OTHER PUBLICATIONS

Search Report issued by the European Patent Office, dated Dec. 13, 2019, for Application No. EP19195996; 10 pages.
(Continued)

*Primary Examiner* — Michael J Carey
*Assistant Examiner* — Christen A. Sharpless
(74) *Attorney, Agent, or Firm* — Faegre Drinker Biddle & Reath LLP

(57) ABSTRACT

A tip part assembly for an endoscope having a proximal end and a distal end positioned oppositely from the proximal end, the tip part assembly including: a working channel extending in a longitudinal direction extending from the proximal end toward the distal end, and a camera assembly including a flexible printed circuit and a camera module having an image sensor, a lens, and a proximal connection surface, wherein the camera module is positioned above the working channel in a top-down direction providing a lateral direction extending laterally from both the camera module and the working channel, and wherein the flexible printed circuit continues from a connection to the connection surface of the camera module in the lateral direction into a first fold of the flexible printed circuit toward the proximal end of the tip part assembly.

23 Claims, 8 Drawing Sheets

(30) Foreign Application Priority Data

Sep. 6, 2019 (EP) .................................... 19195996
Sep. 6, 2019 (EP) .................................... 19195998

(51) Int. Cl.

| | | |
|---|---|---|
| A61B 1/005 | (2006.01) | |
| A61B 1/015 | (2006.01) | |
| A61B 1/018 | (2006.01) | |
| A61B 1/05 | (2006.01) | |
| A61B 1/06 | (2006.01) | |
| A61B 1/07 | (2006.01) | |
| A61B 1/307 | (2006.01) | |
| B29K 105/00 | (2006.01) | |
| B29L 31/00 | (2006.01) | |

(52) U.S. Cl.
CPC ........ *A61B 1/0011* (2013.01); *A61B 1/00124* (2013.01); *A61B 1/009* (2022.02); *A61B 1/015* (2013.01); *A61B 1/018* (2013.01); *A61B 1/051* (2013.01); *A61B 1/0684* (2013.01); *A61B 1/07* (2013.01); *A61B 1/307* (2013.01); *B29K 2105/0097* (2013.01); *B29L 2031/7546* (2013.01)

(58) Field of Classification Search
CPC ......... A61B 1/005; A61B 1/015; A61B 1/018; A61B 1/0684; A61B 1/07; A61B 1/307; A61B 1/05; B29C 45/14467; B29K 2105/0097; B29L 2031/7546
USPC .......................................................... 600/104
See application file for complete search history.

(56) References Cited

U.S. PATENT DOCUMENTS

| | | | |
|---|---|---|---|
| 5,951,464 A | 9/1999 | Takahashi et al. | |
| 7,662,094 B2 | 2/2010 | Iddan | |
| 7,833,151 B2 | 11/2010 | Khait et al. | |
| 8,414,480 B2 | 4/2013 | Kendale et al. | |
| 8,485,966 B2 | 7/2013 | Robertson | |
| 9,125,582 B2 | 9/2015 | Petersen | |
| 9,158,037 B2 | 10/2015 | Otsuka et al. | |
| 9,622,649 B2 | 4/2017 | Lin | |
| 9,814,371 B2 | 11/2017 | Segi et al. | |
| 9,866,738 B2 | 1/2018 | Kojima | |
| 10,025,088 B2 | 7/2018 | Handte et al. | |
| 10,188,275 B2 | 1/2019 | Sonnenschein et al. | |
| 2002/0193663 A1 | 12/2002 | Matsuura | |
| 2003/0113642 A1 | 6/2003 | Kami et al. | |
| 2004/0027459 A1 | 2/2004 | Segawa et al. | |
| 2004/0242963 A1 | 12/2004 | Matsumoto et al. | |
| 2005/0143659 A1 | 6/2005 | Saiga | |
| 2005/0222499 A1 | 10/2005 | Banik et al. | |
| 2005/0277340 A1 | 12/2005 | Gordon et al. | |
| 2006/0264704 A1 | 11/2006 | Fujimori et al. | |
| 2007/0027360 A1 | 2/2007 | Mitsuya | |
| 2007/0249907 A1 | 10/2007 | Boulais et al. | |
| 2008/0132760 A1 | 6/2008 | Takeuchi | |
| 2008/0242935 A1 | 10/2008 | Inoue | |
| 2008/0266441 A1 | 10/2008 | Ichimura | |
| 2008/0312504 A1 | 12/2008 | Kimoto | |
| 2009/0012358 A1 | 1/2009 | Ichihashi et al. | |
| 2009/0259101 A1 | 10/2009 | Unsai | |
| 2009/0260553 A1 | 10/2009 | Skovbo | |
| 2009/0295913 A1 | 12/2009 | Sato et al. | |
| 2010/0016667 A1 | 1/2010 | Segawa et al. | |
| 2010/0185052 A1 | 7/2010 | Chang | |
| 2011/0118549 A1 | 5/2011 | Han | |
| 2011/0288372 A1 | 11/2011 | Petersen | |
| 2012/0197081 A1 | 8/2012 | Kimura | |
| 2012/0220825 A1* | 8/2012 | Kimura ............... A61B 1/00124 |
| | | | 600/109 |
| 2012/0229615 A1* | 9/2012 | Kirma ................ A61B 1/00096 |
| | | | 348/E7.085 |
| 2013/0041223 A1 | 2/2013 | Kato | |
| 2013/0060083 A1 | 3/2013 | Oku | |
| 2013/0150667 A1 | 6/2013 | Mitamura et al. | |
| 2013/0172678 A1 | 7/2013 | Kennedy et al. | |
| 2013/0175720 A1 | 7/2013 | Otsuka et al. | |
| 2013/0271588 A1* | 10/2013 | Kirma ................ A61B 1/00096 |
| | | | 348/76 |
| 2014/0073853 A1 | 3/2014 | Swisher et al. | |
| 2014/0100421 A1 | 4/2014 | Dejima et al. | |
| 2014/0142384 A1 | 5/2014 | Chung et al. | |
| 2014/0210976 A1 | 7/2014 | Lin | |
| 2014/0330081 A1 | 11/2014 | Imai | |
| 2015/0005580 A1* | 1/2015 | Petersen .............. A61B 1/0676 |
| | | | 600/112 |
| 2015/0062316 A1 | 3/2015 | Haraguchi et al. | |
| 2015/0094534 A1 | 4/2015 | Yamada | |
| 2015/0148603 A1 | 5/2015 | Holste | |
| 2015/0312457 A1 | 10/2015 | Kojima | |
| 2015/0358518 A1 | 12/2015 | Ishii et al. | |
| 2015/0378144 A1 | 12/2015 | Handte et al. | |
| 2016/0029879 A1 | 2/2016 | Ishikawa | |
| 2016/0051222 A1 | 2/2016 | Imahashi | |
| 2016/0209637 A1 | 7/2016 | Fujimori | |
| 2016/0235629 A1 | 8/2016 | Allyn et al. | |
| 2016/0287060 A1* | 10/2016 | Usuda .................... A61B 1/051 |
| 2016/0313552 A1 | 10/2016 | Tomatsu | |
| 2017/0035279 A1 | 2/2017 | Fujii | |
| 2017/0108691 A1 | 4/2017 | Kitano | |
| 2017/0108692 A1 | 4/2017 | Kitano et al. | |
| 2017/0123200 A1 | 5/2017 | Suyama | |
| 2017/0245734 A1 | 8/2017 | Kaneko | |
| 2017/0251914 A1 | 9/2017 | Kitano | |
| 2017/0325663 A1 | 11/2017 | Levy et al. | |
| 2018/0070803 A1 | 3/2018 | Mikami | |
| 2018/0153381 A1* | 6/2018 | Wei .................... A61B 1/00002 |
| 2018/0160893 A1 | 6/2018 | Truckai et al. | |
| 2018/0168041 A1* | 6/2018 | Govrin ................ A61B 1/0684 |
| 2018/0242822 A1 | 8/2018 | Hamazaki | |
| 2018/0317756 A1 | 11/2018 | Unsai | |
| 2019/0150711 A1 | 5/2019 | Chiu et al. | |
| 2019/0191968 A1 | 6/2019 | Tsumaru | |
| 2019/0282070 A1 | 9/2019 | Vilhelmsen et al. | |
| 2020/0163535 A1 | 5/2020 | Sekido | |
| 2020/0178766 A1 | 6/2020 | Ichihara | |
| 2020/0192078 A1 | 6/2020 | Spring et al. | |
| 2020/0225461 A1 | 7/2020 | Aizenfeld et al. | |
| 2020/0288953 A1 | 9/2020 | Sørensen et al. | |
| 2020/0297193 A1 | 9/2020 | Takahashi et al. | |
| 2021/0068634 A1 | 3/2021 | Sørensen | |
| 2021/0068640 A1 | 3/2021 | Sørensen | |
| 2021/0068642 A1 | 3/2021 | Sørensen | |
| 2021/0105386 A1 | 4/2021 | Satake | |
| 2021/0153729 A1 | 5/2021 | Kirma et al. | |
| 2022/0061630 A1* | 3/2022 | Yan ......................... H05K 1/182 |

FOREIGN PATENT DOCUMENTS

| | | | | |
|---|---|---|---|---|
| DE | 102010034623 A1 | 2/2012 | | |
| EP | 0306723 B1 | 3/1989 | | |
| EP | 0754429 B1 | 9/2004 | | |
| EP | 2110069 B1 | 3/2011 | | |
| EP | 2677736 A1 | 3/2013 | | |
| EP | 2594307 A1 | 5/2013 | | |
| EP | 2677736 A1 * | 12/2013 | ........... A61B 1/0011 |
| EP | 2692277 A1 | 2/2014 | | |
| EP | 2913850 A1 | 9/2015 | | |
| EP | 2692227 B1 | 8/2018 | | |
| JP | 2004008638 A | 1/2004 | | |
| JP | 2008118568 A | 5/2008 | | |
| JP | 2010005277 A | 1/2010 | | |
| JP | 2011200397 A | 10/2011 | | |
| JP | 2011200399 A | 10/2011 | | |
| JP | 2011217887 A | 11/2011 | | |
| JP | 2012-201065 A | 10/2012 | | |
| JP | 2015002805 A | 1/2015 | | |
| JP | 2015058118 A | 3/2015 | | |
| JP | 5977892 B1 | 8/2016 | | |

(56) References Cited

FOREIGN PATENT DOCUMENTS

| | | | |
|---|---|---|---|
| JP | 2016221316 A | | 12/2016 |
| JP | 2017074207 A | | 4/2017 |
| JP | 2018093907 A | * | 6/2018 |
| WO | 01/10295 A1 | | 2/2001 |
| WO | 2008/023965 A1 | | 2/2008 |
| WO | 2010066790 A1 | | 6/2010 |
| WO | 2014203604 A1 | | 12/2014 |
| WO | 2018/022402 A1 | | 2/2018 |
| WO | 2018/022418 A2 | | 2/2018 |
| WO | 2019138462 A1 | | 7/2019 |

OTHER PUBLICATIONS

Search Report issued by the European Patent Office, dated Feb. 1, 2021, for related Application No. EP20191424.9; 9 pages.
Extended search report in European Application No. 1919 5995, dated Dec. 13, 2019.
Extended search report in European Application No. 1919 5989, dated Jan. 3, 2020.
Extended search report in European Application No. 1919 5998, dated Dec. 2, 2019.
Examination Report issued in EP 19 195 998.0, dated Jun. 28, 2023, 5 pages.
Examination Report issued in EP 20 191 424.9, dated Jul. 5, 2023, 5 pages.

* cited by examiner

TIP PART ASSEMBLY FOR AN ENDOSCOPE

CROSS-REFERENCE TO RELATED APPLICATIONS

The present application claims priority from, and the benefit of, European Patent Application Nos. 19195989.9, 19195995.6, 19195996.4, and 19195998.0, filed Sep. 6, 2019, which applications are incorporated by reference herein in their entirety.

Commonly owned U.S. patent applications Ser. Nos. 17/013,519, 17/013,445, and 17/013,488, filed concurrently with the present application, claim priority from European Patent Application Nos. 19195989.9, 19195995.6, 19195996.4, and 19195998.0, and are incorporated by reference herein in their entirety.

TECHNICAL FIELD

The present disclosure relates to endoscopes and more specifically to a tip part assembly for an endoscope.

BACKGROUND

Endoscopes are well known for visually inspecting places that are difficult to access, such as human body cavities. Typically, the endoscope comprises an elongated insertion tube with a handle at the proximal end, as seen from the operator, and visual inspection means, such as a built-in camera, at the distal end of the elongated insertion tube. This definition of the terms distal and proximal, i.e. proximal being the end closest to the operator and distal being the end remote from the operator, as used herein for endoscopes in general, is adhered to in the present specification.

As the name indicates, endoscopes are used for seeing inside things, such as lungs or other human body cavities of a patient. Modern endoscopes are therefore typically equipped with a light source and a vision receptor including a vision sensor, such as a camera or an image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode, LED, or an optical fibre, may provide illumination.

Electrical wiring for the camera and other electronics, such as LED lighting accommodated in the tip part assembly at the distal end, run along the inside of the elongated insertion tube from the handle to the tip part assembly. Instead of using cameras, endoscopes may also be fibre-optic, in which case the optical fibres run along the inside of the elongated insertion tube to the tip part assembly. For some applications, a working or suction channel may run along the inside of the insertion tube from the handle to the tip part assembly, e.g. allowing liquid to be removed from the body cavity or allowing for insertion of surgical instruments or the like, into the body cavity. The suction channel may be connected to a suction connector, typically positioned at a handle at the proximal end of the insertion tube. For other applications, the working or suction channel may be omitted.

In order to be able to manoeuvre the endoscope inside the body cavity, the distal end of the endoscope may comprise a bending section with increased flexibility, e.g. an articulated tip part assembly allowing the operator to bend this section. Typically, this is done by tensioning or slacking steering wires also running along the inside of the elongated insertion tube from the articulated tip part assembly to a control mechanism of the handle.

A general desire in the field of endoscopy is to electrically insulate the insertion tube, and thus especially the tip part assembly, from the outside, so as to mitigate the risk of an insulation breakdown and a resulting excessive leakage current.

Another general desire in the field of endoscopy is to provide a tip part assembly which is liquid-sealed, so as to mitigate liquid ingress into the tip part assembly, and specifically into any electrical or optical components of the tip part assembly.

For some types of endoscopes, such as urethroscope, there is a desire to provide the tip part assembly of the endoscope with a smaller diameter or cross sectional extent, especially where the tip part assembly is to be inserted into narrower body cavities. In very narrow body cavities, even a reduction of 1 mm or less in the cross-sectional extent of a tip part assembly can have a noticeable effect on the comfort of the patient and may even make it possible to reach body areas not otherwise accessible. Providing a small size of the tip part assembly can especially be a challenge in cases where the endoscope comprises both a camera and a working channel extending through the tip part assembly since the camera and working channel are positioned one above the other within the tip part assembly, which takes up space in a radial direction of the tip part assembly.

In some prior art tip part assemblies, a camera assembly with a flexible printed circuit (FPC) and a camera module are included. The FPC is connected to a connection surface proximally of or at a rear side of the camera module. The camera module comprises an image sensor and a lens stack positioned distally or in front of the image sensor. When a working channel is included as well, the camera module is positioned above the working channel within a housing with a typically circular-cylindrical circumferential outer surface. The FPC lies side-by-side with and is connected to the connection surface of the camera module. From this connection, the FPC extends upwardly, i.e. away from the working channel, into a fold toward a proximal end of the housing. Further towards or beyond a proximal end of the housing where there is room proximally of or behind the connection surface of the camera module, the FPC includes electrical components for the camera module and potentially any LEDs.

It is therefore desirable to provide a tip part assembly with a small outer diameter for an endoscope, such as a urethroscope, having electrically insulating properties and with a mechanically stable printed circuit.

On this background it is desirable to provide an improved tip part assembly for an endoscope, which at least mitigates some of the abovementioned drawbacks.

SUMMARY

A first aspect of this disclosure relates to a tip part assembly for an endoscope, the tip part assembly having a proximal end for being connected to other parts of the endoscope and a distal end positioned oppositely from the proximal end for forming a distal end of the endoscope, the tip part assembly comprising: a working channel extending in a longitudinal direction, the longitudinal direction extending from the proximal end towards the distal end of the tip part assembly, and a camera assembly including a flexible printed circuit and a camera module, the camera module including an image sensor and a lens stack and extending in the longitudinal direction, the camera module comprising a proximal connection surface, wherein the camera module is positioned above the working channel in a top-down direction so that a lateral direction extends laterally from both the camera module and the working channel, wherein the flexible printed circuit from a connection of the flexible printed circuit to the connection surface of the camera module continues in the lateral direction beyond the connection surface into a first fold of the flexible printed circuit towards the proximal end of the tip part assembly, wherein the first fold of the flexible printed circuit is arranged proximally of the camera module connection surface.

Alternatively, a tip part assembly for an endoscope according to the first aspect comprises a proximal end for being connected to other parts of the endoscope and a distal end positioned oppositely from the proximal end for forming a distal end of the endoscope, the tip part assembly comprising: a working channel extending in a longitudinal direction, the longitudinal direction extending from the proximal end towards the distal end of the tip part assembly, and a camera assembly including a flexible printed circuit and a camera module, the camera module including an image sensor and a lens stack and extending in the longitudinal direction, the camera module comprising a proximal connection surface, wherein the camera module is positioned above the working channel in a top-down direction so that a lateral direction extends laterally from both the camera module and the working channel, wherein the flexible printed circuit from a connection to the connection surface of the camera module continues in the lateral direction beyond the connection surface into a first fold of the flexible printed circuit towards the proximal end of the tip part assembly.

It has been realized that in the above mentioned prior art tip part assemblies including a camera assembly and a working channel, a lateral volume of the housing may be used for a proximally directed fold or bend of the FPC. This volume is located laterally of or at a side of the camera module and of the working channel positioned one above the other. So, instead of folding the FPC in a top volume of the housing as in the prior art, which means that a top volume of the housing above a top level of the camera module must provide room for the FPC fold, according to the present disclosure, the FPC is folded in a volume or spacing laterally of the camera module and working channel. This means that the mentioned top volume of the housing is not necessary and can be dispensed with or be reduced. This again means that the extent of the housing in a top-down direction can be reduced. This is due to the top-down direction typically being decisive for the necessary diameter or cross-sectional extent of the housing since there is more room at the lateral side of the camera module and working channel. According to the present disclosure, the fold of the FPC is located in the volume of the housing at the lateral side of the camera module and FPC where there is typically more room. Therefore, the diameter or the cross-sectional extent of the housing and thus the tip part assembly can therefore be reduced. This reduction can be from about 0.1 and up to 1 mm or more. Hereby, a patient's comfort during an endoscopy procedure may be improved, and the tip part assembly may even provide access to body areas not otherwise accessible. It has been shown that an outer diameter of the circumferential wall of the tip part assembly of less than 3 mm or even smaller may be achieved.

Another advantage may be that a larger fold radius of the fold may be provided by the arrangement of the FPC at the lateral side of the camera module the FPC, thus potentially reducing the risk that the FPC breaks at the fold.

The term "fold" as used herein may alternatively be denoted "bend". Similarly, the term "folding" may alternatively be denoted "bending".

In such a tip part assembly, a risk of electrical conduction from the electronics inside a housing, such as the FPC, and through the housing to the patient may be mitigated in use, as the FPC may be positioned with at a distance from the housing. The material thickness necessary for the housing material to provide sufficient electrically insulating properties, which may impact the tip part assembly cross-section or diameter, may be reduced to be generally of a size suitable for certain types of endoscopes, such as urethroscopes. Another advantage may be that the risk that the FPC at least partly breaks when bending and/or folding this or that the fold of the FPC gets in physical contact with the housing and at least partly breaks due to wear may be mitigated.

An outer diameter of a circumscribed circle in a cross-section of the tip part assembly may be reduced compared to a tip part assembly with an upwardly extending FPC and fold. Thus, the inner and outer cross-section and/or diameter of a housing, where such is provided, may be reduced, in turn allowing for a small tip part assembly.

The term "endoscope" may be defined as a device suitable for examination of natural and/or artificial body openings, e.g. for exploration of a lung cavity. Additionally, or alternatively, the term "endoscope" may be defined as a medical device.

Flexible printed circuits (FPCs) or flex prints are well-known electronic items that can be manufactured by technologies such as flexible electronics or flex circuits. The FPC may, throughout this specification, be a single- or double-sided flexible circuit or a rigid-flex circuit, and may comprise one or more layers of conductive material and two or more layers of insulating material, and/or may be a flexible flat cable having one or more conductors. In some embodiments, the FPC may be connected to a second flexible printed circuit and/or to a printed circuit board (PCB), e.g. comprising one or more cupper layers and one or more layers of insulating materials, such as layers of a FR-4 (flame retardant) composite material.

FPCs can be considered a type of PCBs in which the carrier medium is more flexible and less elastic than in traditional, rigid PCBs, allowing the FPC to be folded and to flex during use. In FPCs, electronic devices are typically mounted on flexible plastic carrier materials or substrates. Flex circuits can be printed circuits on polyester. Other processes and materials for manufacture of FPCs are also known in the art.

The first fold may be a first fold of several folds of the FPC. The first fold may be the first fold which the FPC extends into when continuing in the lateral direction beyond the camera module connection surface. The first fold may, alternatively or additionally, be a first folded portion of the FPC, potentially a first folded portion of a portion of the FPC.

The first fold may be arranged proximally of the camera module connection surface in the longitudinal direction.

In some embodiments, the entire first fold may be arranged proximally of the camera module connection surface. Potentially, any additional fold of the FPC may furthermore be arranged proximally of the camera module connection surface.

The FPC may not comprise any folds in the top-down direction.

The entire FPC and/or all parts of the FPC may be arranged proximally of the camera module connection surface.

In some embodiments, the FPC may be arranged so that no part of the FPC is arranged in the top volume and/or at a level above a level of a top surface of the camera module. Alternatively or additionally, the FPC may be arranged so that no part of the FPC is arranged above the camera module in the top-down direction and/or below in the top-down direction. Alternatively or additionally, the FPC may be arranged such that no part of the FPC is arranged laterally of the camera module, e.g. adjacent to the camera module in a lateral direction.

In this specification, a proximal-distal direction may be defined as an axis extending along the parts of the insertion tube of the endoscope. Adhering to the definition of the terms distal and proximal, i.e. proximal being the end closest to the operator and distal being the end remote from the operator. The proximal-distal direction is not necessarily straight, for instance, if the insertion tube is bent, then the proximal-distal direction follows the curvature of the insertion tube. The proximal-distal direction may for instance be a centre line of the insertion tube.

The term "proximally" may throughout this text refer to nearer and/or with shorter distance to the proximal end, potentially in the longitudinal direction. For instance, if a first element is described as being arranged proximally of a second element, the first element may thus be arranged nearer the proximal end, when seen in the longitudinal direction, than the second element. The longitudinal direction may be and/or may be identical to the proximal-distal direction.

The distal end of the tip part assembly may form a distal end of the endoscope.

The camera assembly may be a sub-assembly of the tip part and may comprise a camera housing, in which the camera module with the image sensor and lens stack may be arranged. Outer surfaces of the camera module or a camera module housing of the camera module may be substantially box-shaped and/or parallelepipedal. The camera housing may house at least a part of the lens stack and/or a part of the image sensor.

In some embodiments, the tip part assembly comprises one single camera module. Alternatively or additionally, the tip part assembly comprises one single camera assembly.

The lens stack may be positioned distally of or in front of the image sensor, may include two or more lenses and may include a proximal lens and a distal lens. The camera module may further comprise a lens barrel which may hold and encase the lens stack. The lens stack may be stacked and/or the lens barrel may extend in the longitudinal direction. The connection surface may be positioned proximally of or behind the image sensor. The connection surface may face in a proximal direction. The lens stack or the lens barrel may have a longitudinally extending centre line, which may be, or may be coinciding with, a centre line of the camera module.

The at least one lens, potentially the plurality of lenses, may be of one or more types chosen from the group consisting of: concave, convex, plano-concave, plano-convex, bi-convex, bi-concave.

In some embodiments, the working channel may similarly have a longitudinally extending centre line, which may extent from a proximal end to a distal end of the working channel. The centre line of the working channel may furthermore be parallel to the centre line of the of the camera module and/or the centre line of the insertion tube.

The working channel may be substantially tubular and/or have a circumferentially extending, potentially substantially cylindrical or circular cylindrical, outer wall enclosing a working channel spacing. The working channel may have an inner diameter of 0.8 to 2 mm or 1 to 1.6 mm or 1 to 1.4 mm. A wall thickness of a circumferential wall of the working channel may be 0.1 to 0.5 mm.

The working channel may comprise a chamfered portion, which may face at least a part of the camera assembly. The chamfered portion may, additionally or alternatively, be provided as a canted-off portion, a beveled portion, or the like. The chamfered portion may be abutting at least part of the camera assembly or may be positioned with a distance to the camera assembly.

The chamfered portion may be part of the circumferential wall of the working channel, where a such is provided, or may be formed in one piece with the wall. The wall thickness of the chamfered portion of the circumferential wall may thus be smaller than along at least one other portion of the circumferential wall.

The working channel may allow liquid to be removed from a body cavity and/or allow insertion of surgical instruments or the like into the body cavity. The working channel may be provided as a channel extending from a proximal end of an endoscope to a distal end of the endoscope to guide a tool and/or to provide suction. A connector and/or a connection portion may be provided at the proximal end of the endoscope to allow insertion of a tool into the working channel and/or to allow suction to be applied to the working channel. In some embodiments, the working channel comprises a built-in or integrated tool at or in the distal tip part assembly. Such a tool may be suitable for grabbing, taking, and/or holding elements in a part of a patient, in which the endoscope tip part is arranged during use.

The camera module and the working channel may be positioned side-by-side or bottom-to-top. A top surface of the camera module may be positioned adjacent to and may be abutting or in contact with an inner top surface of the circumferential wall of a housing of the tip part assembly. See further below regarding such a housing. A bottom surface of the working channel may be positioned adjacent to and may be abutting or in contact with an inner bottom surface of the circumferential wall of the housing.

In some embodiments, a top surface of the camera module is positioned adjacent to an inner top surface of the circumferential wall of the housing of the tip part assembly.

The housing of the tip part assembly may be an exterior housing. The working channel and the camera assembly may be at least partly housed in the (exterior) housing.

The (first) fold of the FPC may be positioned adjacent to an inner lateral surface of the circumferential wall of a housing. Alternatively or additionally, the (first) fold of the FPC may be abutting or in contact with the inner lateral surface of the circumferential wall of the housing. A folding radius of the first (and/or second and/or third, as mentioned below) fold may be in the range of 0.2-0.6 mm. In some embodiments, the folding radius may be in the range of 0.3-0.5 mm.

In some embodiments, the first fold of the flexible printed circuit is positioned adjacent to an inner lateral surface of the circumferential wall of the housing.

"Adjacent" may in this text be immediately adjacent. Alternatively or additionally, where two elements are described as adjacent to each other, "adjacent" may involve that no part of the tip part is positioned between the two elements. For instance, where the (first) fold of the FPC is positioned adjacent to an inner lateral surface of a circumferential wall of a tip part housing, the FPC (first) fold may be positioned immediately adjacent to the inner lateral surface and/or with no part of the tip part positioned in between the FPC (first) fold and the circumferential wall. Alternatively or additionally, where two elements are described as adjacent to each other, "adjacent" may involve that the two elements are positioned close to each other, such as at a distance smaller than a circumscribed circle of a cross-section of one or both the elements, and/or such as less than 2 mm, less than 1 mm, less than 0.8 mm, less than 0.6 mm, less than 0.4 mm, and/or less than 0.2 mm.

The connection surface of the camera module may comprise one or more connection points for electrical connection with the FPC. The FPC may, at a first portion thereof, comprise one or more connection points for being electrically connected with the connection points of the connection surface of the camera module. The FPC may be electrically connected to the one or more connection points of the camera module connection surface by soldering and/or by anisotropic conductive adhesives (ACA), such as anisotropic conductive film (ACF) or anisotropic conductive paste (APC) bonding. The electrical connection may comprise electrical communication, e.g. by means of varying voltages, electric potentials and/or currents being applied to and/or running through, respectively, the one or more connection points. Alternatively, or in combination therewith, the electrical connection may comprise supplying a supply voltage, such as a V+ and V− connection, to the camera module.

The connection surface of the camera module may lie in a connection surface plane. The first fold of the FPC may be arranged proximally of the connection surface plane.

In some embodiments, the flexible printed circuit continues from the connection to the connection surface and continues towards the proximal end into a first fold towards the proximal end of the tip part assembly. The flexible printed circuit may alternatively or additionally directly continue towards the proximal end. Additionally or alternatively, the flexible printed circuit may continue away from the connection surface plane.

The camera assembly may comprise a mounting frame. The mounting frame may support and/or secure one or more in the group consisting of: the printed circuit board, one or more light sources, such as light emitting diodes (LEDs) potentially provided at the distal end of the tip part assembly, the lens barrel, and the image sensor.

The FPC may include one or more portions leading to and establishing an electrical connection with respective LED(s) of the tip part assembly. The LED(s) may be positioned within a volume or spacing of the tip part assembly, or a housing thereof. The FPC may comprise a first, second, and third LED portion. The first LED portion of the FPC may be extending from and connected to and/or formed in one piece with a portion, i.e. a second portion, of the FPC, which continues towards the proximal end of the tip part assembly. Alternatively, or in combination therewith, the first LED portion may be extending from and connected to and/or formed in one piece with the first portion of the FPC, which is connected to the connection surface of the camera module.

The first LED portion may continue to the second LED portion and into the third LED portion, which may be electrically connected to one or more LEDs. The first, second and third LED portions may each comprise one or more folds or bends, and/or may be interconnected by one or more folds or bends.

The third LED portion may be electrically connected to the at least one LED by soldering and/or by anisotropic conductive adhesives (ACA), such as anisotropic conductive film (ACF) or anisotropic conductive paste (APC) bonding.

The LEDs may be arranged at the distal end of the tip part assembly or abutting one or more light guides (see description below) arranged at the distal end of the tip part assembly, and may have a connection surface extending substantially in parallel or in parallel to the connection surface of the camera module. The third LED portion of the FPC may extend in parallel or substantially in parallel to the connection surface of the at least one LED. The LEDs may be arranged beside the camera module in the lateral direction, and the first and/or second and/or third LED portions may be extending in the lateral direction. Where a lateral spacing is provided in a housing, the first and/or second and/or third LED portions may be arranged in the lateral spacing.

The tip part assembly may comprise one or more LED holders. The LED holder(s) may comprise at least one first portion extending in or substantially in the longitudinal direction. The LED holder first portion may abut the third LED portion of the FPC so as to support the third LED portion and/or the LED. The LED holder may, where e.g. two or more LEDs and two or more third LED portions are provided, comprise a second portion, which may abut and support the third LED portion of the FPC and/or the LED. The LED holder first and second portions may be interconnected by at least one interconnecting portion of the LED holder. The interconnecting portion may be arranged proximally, i.e. further towards the proximal end of the tip part assembly, of the first LED portion of the FPC. The LED holder may be made from a material comprising or consisting of a polymer, such as polyethylene (PE), acrylonitrile butadiene styrene (ABS), or the like, and may be manufactured by means of extrusion, molding, and/or 3D-printing. The LED holder may be manufactured in one piece or may comprise several pieces adjoined, e.g. by means of an adhesive.

The tip part assembly may also include one or more light guides for guiding light from respective LED(s) to e.g. a front or distal end surface or end wall of the tip part assembly and/or a housing thereof. One or more light guides may be in one piece, potentially molded in one piece with, a housing of the tip part assembly. The light guide(s) may extend from the distal end of the tip part assembly to a respective LED or a respective set of LEDs. In some embodiments, the light guides are made from a transparent material. The light guide(s) may be molded and/or may comprise a portion abutting the camera module and/or be arranged in front of the lens stack.

The LEDs may comprise a light emitting surface. The light emitting surface(s) may emit light in the proximal-distal direction. The light emitting surface(s) may be positioned in abutment with a housing, where this is provided, or in abutment with one or more light guides.

An exterior flexible sleeve may be provided to extend around at least part of the tip part assembly, potentially of a housing thereof and/or around at least part of an insertion tube of the endoscope A maximum extent in the longitudinal direction from the distal end of the tip part assembly to a proximal end of the housing or FPC is in some embodiments 12, 10 or 8 mm.

The longitudinal direction may extend at a substantially right angle or at a right angle to the top-down and lateral directions, and the top-down and lateral directions may extend at a substantially right angle or at a right angle to each other.

A plane of symmetry may pass through a longitudinally extending centre line of the working channel and through a longitudinally extending centre line of the camera module, wherein the flexible printed circuit from the connection to the connection surface of the camera module may extend approximately perpendicularly to the plane of symmetry.

In some embodiments, the camera module extends perpendicularly to the plane of symmetry.

Electrical components may be arranged on portions of the FPC extending on both sides of the symmetry plane, in turn allowing for a spatially compact arrangement of electrical components. In some embodiments, an interconnecting portion of the FPC may be provided, where the FPC interconnecting portion interconnects the portions on both sides of the symmetry plane. Thus, the FPC interconnecting portion may intersect the symmetry plane.

Electrical components may be passive components, such as capacitors, resistors or inductions, semiconductors, such as diodes or transistors, or wires, such as single wires, wire bundles, or FFCs, or any combination thereof.

The first fold may bend or fold with an angle from 90 to 180 degrees. This folding angle may in some embodiments be in the range from 120 to 150 degrees, such as from 130 to 140 degrees.

The tip part assembly may include a housing having a circumferentially extending outer surface for facing the environment. The outer surface may enclose a volume and may extend in a longitudinal direction between a proximal end and a distal end of the housing. The working channel may be at least partly housed in the housing and may comprise an opening in a distal surface of the housing. The camera assembly may be at least partly housed in the housing.

The terms "circumferentially extending outer surface" and "circumferential wall" may be used interchangeably throughout this text. Hence, the housing may have a circumferential wall for facing the environment.

The working channel may, alternatively or additionally, be partly or entirely housed in the housing. The camera assembly may be partly or entirely housed in the housing.

The camera module and/or the FPC may be at least partly or fully shielded electrically and/or from liquid from the body of a patient when the endoscope is in use. This may, in turn, mitigate a risk of failure due to electrical short-circuiting as well as a risk of electrically shocking a patient on which the endoscope is used.

Furthermore, an advantage of the tip part assemblies according to this disclosure may be that the need for material of the housing to provide electrical insulation may be reduced by the arrangement of the FPC. By the fold of the FPC being arranged at the lateral side of the camera module and working channel, i.e. where there is more room than in the top volume of the housing, the FPC may be positioned further from the housing wall than if arranged in the top volume, thereby using the dielectric properties of the air or of a material arranged between the FPC and the housing wall, such as a potting material where such is provided in the housing.

In some embodiments a potting material, such as an adhesive, may be provided in the housing. The potting material may fill out any or parts of a spacing between the components, e.g. the working channel, the camera module, and/or the FPC, or the sections thereof arranged inside the housing.

The housing may be tubular and/or cylindrical or substantially cylindrical and/or circular cylindrical or substantially circular cylindrical. The working channel and camera assembly may be at least partly housed in the housing. The working channel or a part thereof may be in one piece with the housing and/or may be provided as a separate part. The working channel may comprise a first portion potentially provided in one piece with the housing, and a second portion interconnected with the first portion. The second portion may be provided as a flexible tube and may be interconnected to the first portion by means of an adhesive.

The housing may provide electrical insulation and/or water tightness around the FPC and electrical connections within the housing and may form a mold or container for adhesive and/or potting material poured or injected into the housing. The housing may ensure that a minimum insulation thickness is present on one or more sides or all outer surfaces of the tip part assembly. If an adhesive or a potting material is present in the housing, this may provide greater robustness, mechanical stability and/or rigidity of the tip part, and/or better attachment/fixation of components within the housing. This may be advantageous since wires or cables may be pulled during operation of the endoscope, pulling also in the FPC, especially during bending of a bending section of the tip part assembly.

Molding of the housing may occur as a two-component molding in which two different materials are molded in the same mold. For example, the end wall of the housing may be molded in a first material, which may be transparent, and the circumferential wall may be molded in a second, different material, which may be non-transparent and may include higher adhesive compatibility with an adhesive or potting material in the housing. Alternatively, the circumferential wall can be manufactured separately from the end wall. For example, the two walls can be molded separately, or the end wall can be molded, and the circumferential wall extruded. In this case, the circumferential wall and the end wall can be adhered to each other by means of an adhesive.

The housing may comprise a tubular wall enclosing a volume, the volume being a spacing within the housing. This spacing may also be defined by a distal end wall of the housing. An opening for the working channel may be provided in the end wall. The camera module and potentially other components of the tip part assembly may be at least partly housed within the spacing and potentially attached, potentially by means of adhesive, to the housing. The housing may be a molded part, and the spacing may be at least partly filled with a hardened adhesive, the hardened adhesive being provided separately from the housing. Alternatively, the housing may take the form of a hardened adhesive in which the camera module and potentially other components may be embedded.

A lateral portion of the volume of the housing may be defined laterally from the camera module and the working channel, the lateral volume extending between the proximal end and the distal end of the housing. An FCP first portion or connections thereof may be electrically connected to the at least one connection of the connection surface. The FPC first portion may be positioned face-to-face with the connection surface and extending into a second portion of the FCP. The FPC second portion may extend laterally from the first portion beyond the connection surface and into the lateral spacing portion. The second portion may comprise the first fold, the first fold being positioned in the lateral spacing portion.

The housing may be an outer or exterior housing which may be exterior with respect to elements housed or enclosed therein, such as the camera module, the FPC, wires, electrical components, LEDs, and the like.

The circumferential wall may have a longitudinal centre axis extending between a distal end and a proximal end of the housing. The working channel or a part thereof may have a longitudinal centre axis extending in parallel with or substantially in parallel with a centre axis of the housing, and the camera module may have a longitudinal centre axis extending substantially in parallel with or in parallel with the longitudinal centre axis of the housing. A centre plane of the tip part assembly may substantially coincide with the longitudinal centre axis of the camera module and the longitudinal centre axis of the working channel. The fold of the FPC may be folded about a folding axis lying in a plane in parallel with or substantially parallel with this centre plane.

In some embodiments, the camera module has a longitudinal centre axis extending in parallel or substantially in parallel with a longitudinal centre axis of the housing. A centre plane of the tip part assembly may coincide with a longitudinal centre axis of the camera module and the longitudinal centre axis of the working channel. The fold of the FPC may be folded about a folding axis lying in a plane parallel with the centre plane.

A lateral portion of the volume of the housing may be defined laterally from the camera module and the working channel. The lateral volume or a part thereof may extend between the proximal end and the distal end of the housing. An FPC first portion or connections thereof may be electrically connected to the at least one connection of the connection surface. The first portion may be positioned face-to-face with the connection surface and may extend into a second portion of the FPC as mentioned above. The second portion may extend laterally from the first portion beyond the connection surface and into the lateral spacing portion. The second portion may comprise the first fold, and the first fold may be positioned in the lateral spacing portion.

The flexible printed circuit from the connection to the connection surface of the camera module may also extend in an opposite lateral direction beyond the connection surface into a second fold of the flexible printed circuit towards the proximal end of the housing. The opposite lateral direction may extend substantially oppositely to the lateral direction.

Alternatively, the opposite lateral direction may extend oppositely to the lateral direction.

The second fold may be provided in a similar, mirrored manner to the first fold. Any one or more embodiments described above regarding the first fold may also apply to the second fold. The first and second folds may be symmetrical, potentially about a symmetry axis or centre plane as mentioned above. The first and second bends or folds may continue to be connected in a portion of the FPC positioned further proximally or they may extend separately all the way to a proximal end of the FPC.

The tip part assembly may further comprise a support for the flexible printed circuit, and the first fold may be folded about a folding portion of the support. The support may be a support bracket.

Thereby, the FPC may be supported at least at the folds during assembly and/or during use, thus reducing a risk of the FPC breaking and/or having poor electrical conductivity, for instance caused by high resistance or capacitance, due to wear at the fold.

The support may extend in the longitudinal direction. The shape of at least a portion of the support may substantially correspond or correspond to the fold of the FPC. The support or this portion thereof may comprise at least one rounded section, and the rounded section may have a rounding radius corresponding to the folding radius of the FPC fold.

Where two folds of the FPC are present, the same support may be used for both folds. Correspondingly, the support may be T-shaped or substantially T-shaped when seen in the top-down direction, may comprise a support main portion and two folding portions about which the FPC folds may be arranged. The two folding portions may each be rounded when seen in the top-down direction. The two folding portions may be provided as the upper part of the T-shape of the support. The upper part of the T-shaped support may extend in the lateral direction, and the main portion may extend in the longitudinal direction. The support main portion may extend at a substantially right angle or at a right angle to the folding portions. A rounding radius of the two folding portions may correspond to a folding radius of a respective FPC fold and/or an FPC second fold to be arranged along the folding portion. The FPC may follow an outer contour of the support.

Where LED portions of the FPC are provided, a first LED portion may be connected to and/or formed in one piece with a part of the FPC extending along the support and may extend away from the support. Alternatively, or in combination therewith, the first LED portion may be arranged so that at least part of the first LED portion is arranged above and/or below the support main portion. The second LED portion of the FPC may furthermore extend substantially in parallel or in parallel to the support main portion.

The FPC may be attached to a surface of the support to extend along the support. The attachment may be provided by means of an adhesive, such as a non-conducting adhesive.

The FPC may continue or extend further from the first fold into a third fold of the flexible circuit board, and the third fold may fold in a direction opposite to the first fold.

Thereby, a portion of the FPC may extend towards the proximal end allowing for easy guiding of wires, where such are mounted on and/or connected to the FPC.

The FPC may continue or extend further from the second fold into a fourth fold of the flexible circuit board, and the fourth fold may fold in a direction opposite to the first fold.

The lens stack may be positioned distally of or in front of the image sensor and may include two or more lenses, which may include a proximal lens and a distal lens. The camera module may further comprise a lens barrel which holds the lens stack. The lens stack may be stacked in the longitudinal direction, and the lens barrel may extend in the longitudinal direction.

A folding angle of the third fold may be above 0 and up to 90 degrees, such as 30 to 60 degrees, such as 40 to 50 degrees.

An outer maximum extent in the lateral direction of the tip part assembly may be less than 3.3 mm.

This outer maximum extent may a maximum outer diameter of the tip part assembly and/or may be a maximum cross sectional extent. The outer maximum extent may be less than 3.2, 3.1, 3.0. 2.9, 2.8, 2.7, 2.6, or 2.5 mm.

The tip part assembly may further comprise a bending section which may have a distal end segment which may be connected to a housing of the tip part assembly.

The housing may be a housing according to one or more embodiments of the housing as described above.

This may allow for the tip part assembly to be manoeuvred inside the body cavity. Thereby, various places inside the body cavity may be inspected by means of the camera assembly, and/or the working tool or suction may, by means of the working channel, be applied at various places inside the body cavity.

The bending section may comprise a number of hingedly interconnected segments including a distal end segment, a proximal end segment, and a plurality of intermediate segments positioned between the proximal end segment and the distal end segment. At least one hinge member may interconnect adjacent segments with each other. The bending section may be a section allowing the tip part assembly to bend relative to an insertion tube, potentially so as to allow an operator to manipulate the tip part assembly while inserted into a body cavity of a patient. The bending section may be molded in one piece or may be constituted by a plurality of molded pieces.

In some embodiments, the housing may be connected to the distal end segment of the bending section. The housing may be connected to the distal end segment at the proximal end of the housing. The working channel may extend into and/or through the distal end segment and/or the bending section.

A second aspect of this disclosure relates to a method for assembly of a tip part assembly for an endoscope, the tip part assembly having a proximal end for being connected to other parts of the endoscope and a distal end positioned oppositely from the proximal end for forming a distal end of the endoscope, the method comprising the steps of: a) providing a working channel of the tip part assembly, the working channel extending in the longitudinal direction, b) providing a camera assembly of the tip part assembly, the camera assembly including a flexible circuit board and a camera module, the camera module including an image sensor and a lens stack and extending in the longitudinal direction, the camera module comprising a proximal connection surface, c) positioning the camera module above the working channel in a top-down direction so that a lateral direction extends laterally from both the camera module and the working channel, d) connecting the flexible printed circuit to the connection surface of the camera module so that the flexible printed circuit continues in the lateral direction beyond the connection surface, and e) folding a first fold towards the proximal end of the tip part assembly in that part of the flexible printed circuit that continues in the lateral direction beyond the connection surface, wherein the first fold is arranged proximally of the camera module connection surface.

Alternatively a method according to the second aspect may be a method for assembly of a tip part assembly for an endoscope, the tip part assembly having a proximal end for being connected to other parts of the endoscope and a distal end positioned oppositely from the proximal end for forming a distal end of the endoscope, the method comprising the steps of: a) providing a working channel of the tip part assembly, the working channel extending in the longitudinal direction, b) providing a camera assembly of the tip part assembly, the camera assembly including a flexible circuit board and a camera module, the camera module including an image sensor and a lens stack and extending in the longitudinal direction, the camera module comprising a proximal connection surface, c) positioning the camera module above the working channel in a top-down direction so that a lateral direction extends laterally from both the camera module and the working channel, d) connecting the flexible printed circuit to the connection surface of the camera module so that the flexible printed circuit continues in the lateral direction beyond the connection surface, and e) folding a first fold towards the proximal end of the tip part assembly in that part of the flexible printed circuit that continues in the lateral direction beyond the connection surface.

The steps of the method according to the second aspect may be performed in any order, not necessarily in sequence. The steps may be carried out the sequence a), b), c), d), e), or may alternatively be carried out in the sequence a), b), d), e), c), or a), b), d), c), e). Steps a) and b) may be performed simultaneously.

The method may provide identical or similar advantages to the tip part assembly according to the first aspect of this disclosure. Embodiments of the tip part assembly of this method may be the same as described with respect to the tip part assembly according to the first aspect of the disclosure.

In some embodiments, the method comprises the further steps of: f) providing a housing of the tip part assembly, the housing having a circumferentially extending outer surface for facing the environment, the outer surface enclosing a volume and extending in a longitudinal direction between a proximal end and a distal end of the housing, g) positioning the working channel at least partly in the housing so that the working channel comprises an opening in a distal surface of the housing, h) positioning the camera assembly at least partly in the housing.

This embodiment may allow for an easy assembly by the fold being provided in a lateral spacing of the housing. The method may, in turn, mitigate a risk of a FPC breaking or partly breaking at the fold, e.g. due to wear caused by abutment of the FPC with a wall of the housing.

Step e) may in the method occur before, after or during step h). Step f) may be performed simultaneously with steps a) and b). Step g) may be performed before, during or after step h).

In step e), the first fold may be folded about a folding part of a support of the tip part assembly.

The support and/or the folding part thereof may be according to any one of the above embodiments of these.

The folding about the support folding part may be performed or further aided by means of adhesive, such as a non-conductive adhesive, to adhere at least parts of the FPC to the support and/or support folding parts. The adhesive may be applied to the FPC and/or to the support and/or support folding parts before the step of folding the first fold of the FPC.

The folding may, alternatively or additionally, be performed by arranging a distal part of the FPC at a position at the support, so that the FPC follows a contour of the support so as to provide the fold.

Where step e) is performed before step c) and/or step h), the support may further be used to guide the camera module and/or the camera assembly in steps c) and/or h), respectively.

A third aspect of the present disclosure relates to an endoscope comprising a tip part assembly according to the first aspect of the disclosure or a tip part assembly manufactured according to the second aspect of the disclosure.

The endoscope may comprise a control element. The control element may be configured to allow an operator to control a tip part assembly of the insertion tube by at least one steering wire. The control element may allow bending the tip part assembly in at least one direction, potentially in two directions, the two directions potentially being opposite. The control element may be accommodated in an operating handle. The control element may include a lever allowing an operator to control the control element. The lever may extend outwardly from the control element, potentially through an operating handle. The control element may be in the form of a roller or a roller disc.

The endoscope may comprise an operating handle. The operating handle may be suitable for allowing an operator to grip and to operate the endoscope, potentially with one hand. The operating handle may comprise a handle housing arranged at a proximal end of the insertion tube. The handle housing may accommodate the control element.

The insertion tube and/or a distal end thereof and/or the tip part assembly thereof may be suitable for insertion into a body cavity, potentially a kidney, through a body opening, potentially a urinary passage or a urethra. The body may be a natural and/or artificial body, potentially a human body. The insertion tube may extend from the operating handle towards a distal end of the endoscope.

Additionally or alternatively, the endoscope may form part of a system for visually inspecting inaccessible places such as human body cavities, the system further comprising a monitor. The endoscope may be connectable to the monitor, and the monitor may allow an operator to view an image captured by the camera assembly of the endoscope.

A person skilled in the art will appreciate that any one or more of the above aspects of this disclosure and embodiments thereof may be combined with any one or more of the other aspects of the disclosure and embodiments thereof.

BRIEF DESCRIPTION OF DRAWINGS

The tip part assemblies and methods will now be described in greater detail based on non-limiting exemplary embodiments and with reference to the drawings, on which.

Similar reference numerals are used for similar elements across the various embodiments and figures described herein.

DETAILED DESCRIPTION

Figure 1A:
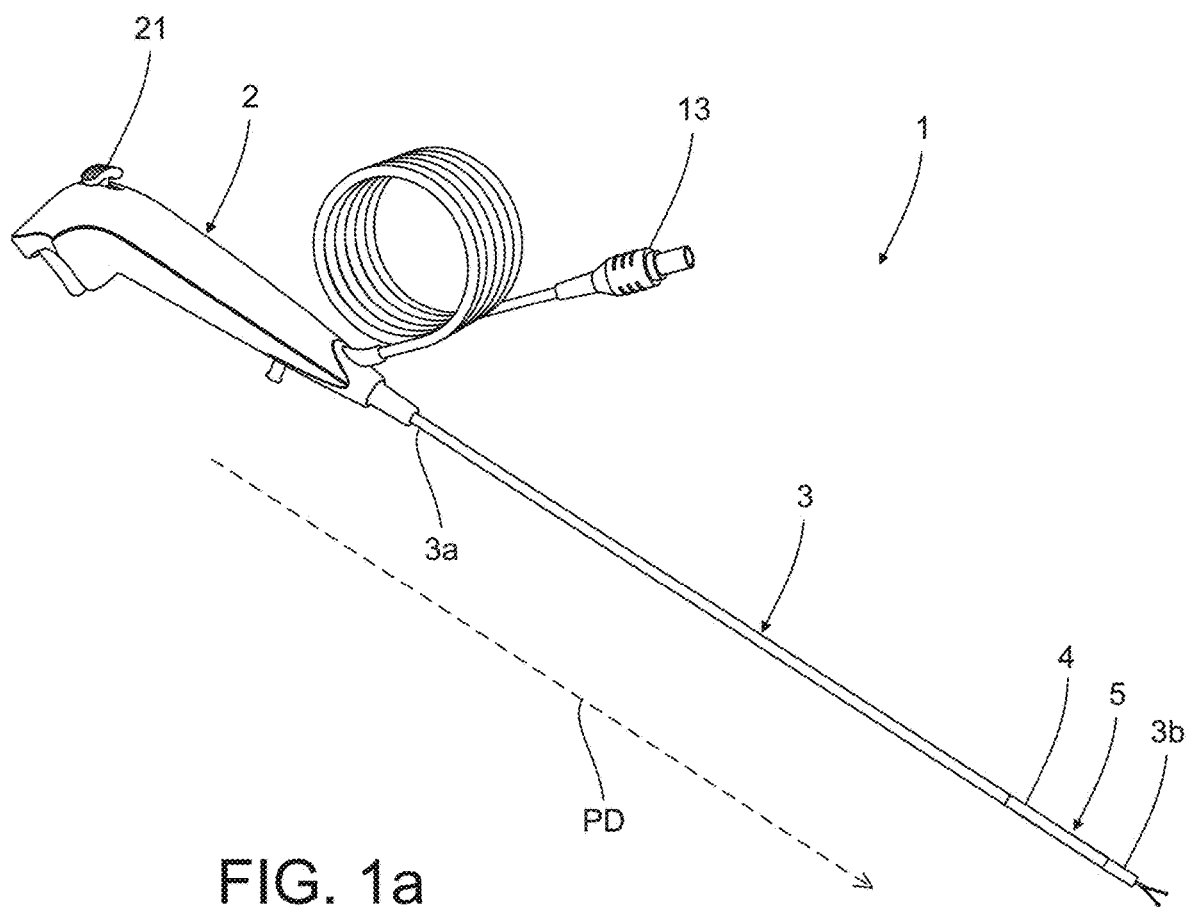
FIG. 1a shows a perspective view of an endoscope in which a tip part assembly according to the present disclosure is implemented.

Referring first to FIG. 1a, an endoscope 1 is shown. The endoscope is disposable, and not intended to be cleaned and reused. The endoscope 1 comprises an elongated insertion tube 3. At the proximal end 3a of the insertion tube 3 an operating handle 2 is arranged. The operating handle 2 has a control lever 21 for maneuvering a tip part assembly 5 at the distal end 3b of the insertion tube 3 by means of a steering wire. A camera assembly 6 is positioned in the tip part 5 and is configured to transmit an image signal through a monitor cable 13 of the endoscope 1 to a monitor 11.

Figure 1B:
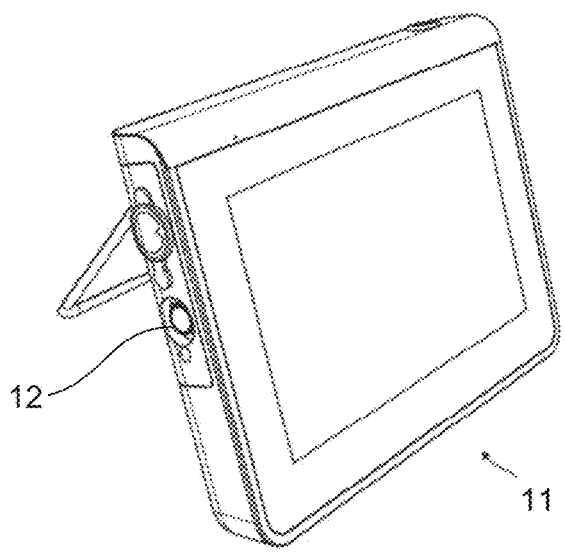
FIG. 1b shows a perspective view of a monitor to which the endoscope of FIG. 1a is connected.

In FIG. 1b, a monitor 11 is shown. The monitor 11 may allow an operator to view an image captured by the camera assembly 6 of the endoscope 1. The monitor 11 comprises a cable socket 12 to which a monitor cable 13 of the endoscope 1 can be connected to establish a signal communication between the camera assembly 6 of the endoscope 1 and the monitor 11.

The proximal-distal direction PD is an axis extending along the parts of the insertion tube 3 of the endoscope 1.

Figure 2A:
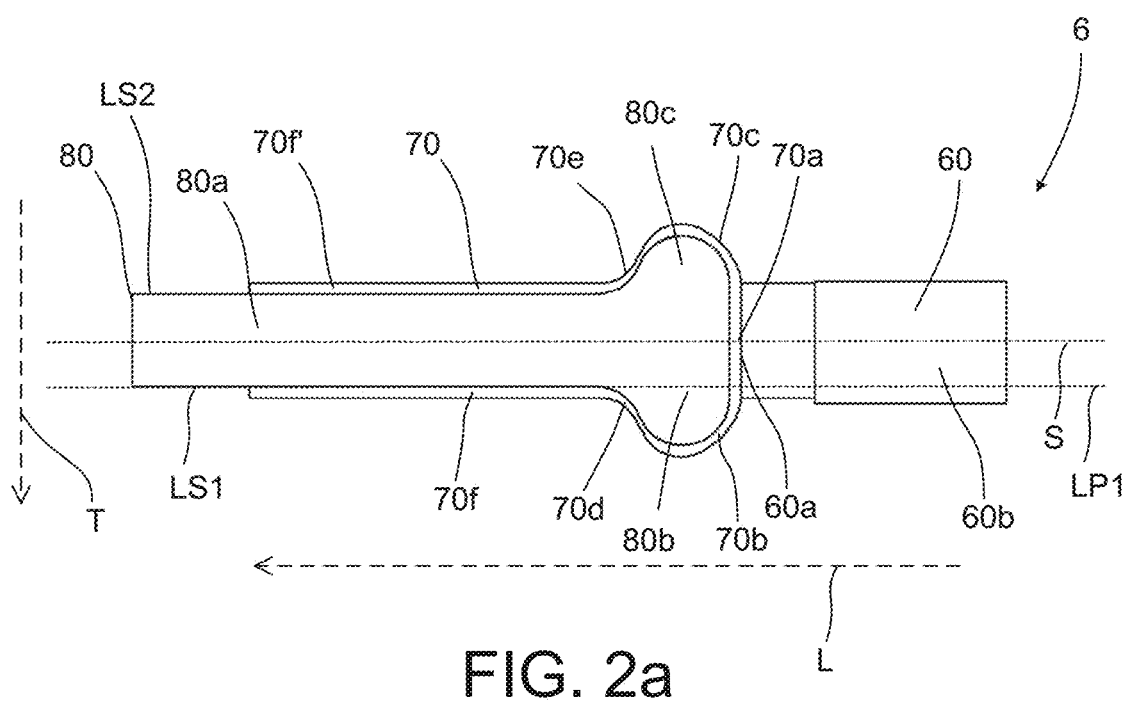
FIG. 2a shows a top view of an embodiment of a camera assembly and a support for the tip part assembly of FIG. 1a, FIG. 2b shows a perspective view of the camera assembly and support of FIG. 2a, FIG. 3a shows a distal end view of the tip part assembly of FIG. 1a, FIG. 3b shows a cross-sectional view of the tip part assembly of FIG. 3a, FIG. 3c shows a second cross-sectional view of the tip part assembly of FIG. 3a, taken orthogonally to the cross-sectional view of FIG. 3b along the line C-C.
Figure 2B:
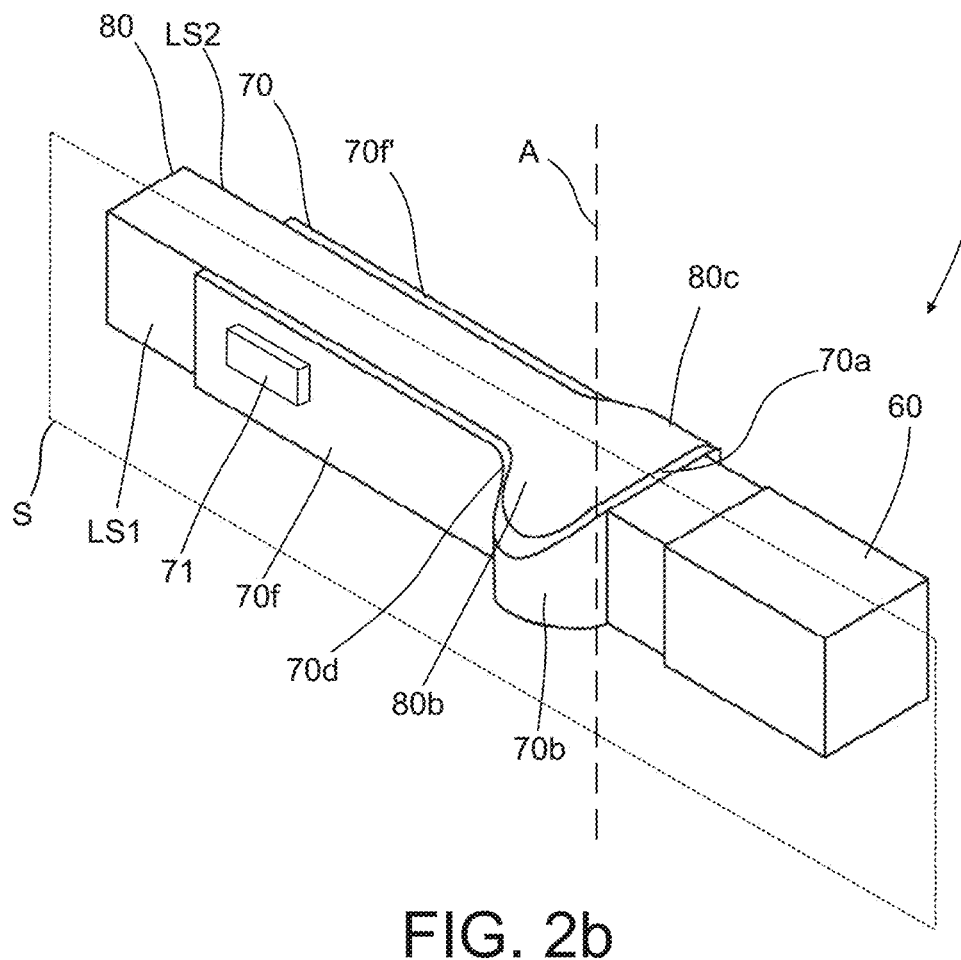

Referring to FIGS. 2a and 2b, a camera assembly 6 and a support 80 is shown. FIGS. 3a-c and 4a show the camera assembly 6 of FIGS. 2a and 2b.

Figure 8:
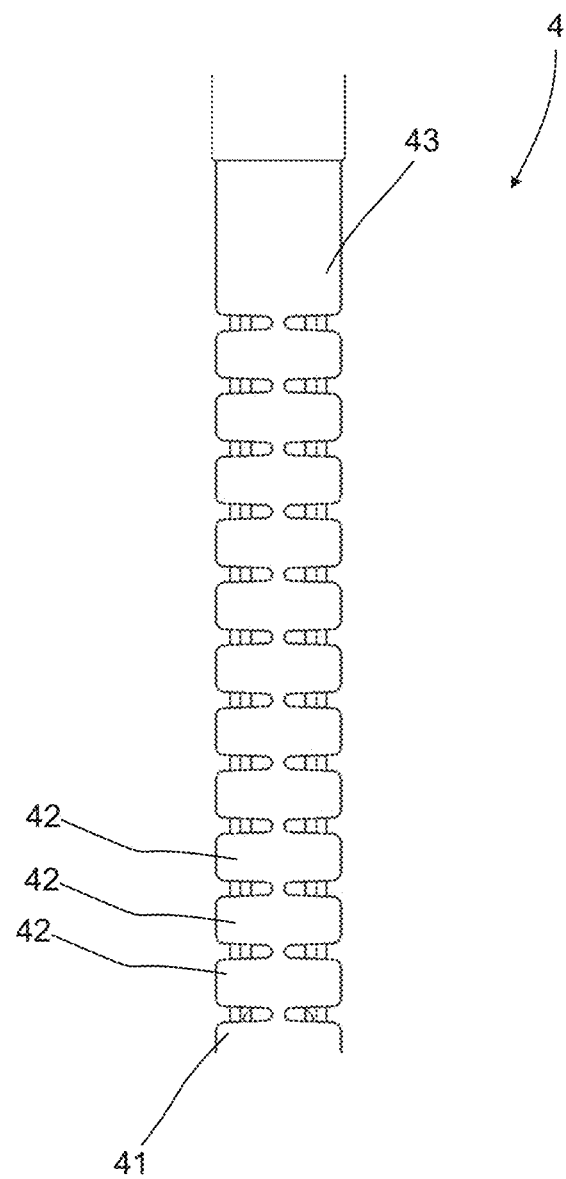
FIG. 8 shows a view of a bending section of the endoscope of FIG. 1a and FIG. 1b.

The tip part assembly has a proximal end for being connected to other parts of the endoscope, such as a bending section 4 as shown in FIG. 8, and a distal end positioned oppositely from the proximal end for forming a distal end 3b of the endoscope 1. The tip part assembly comprises a working channel 7 extending in a longitudinal direction L. The longitudinal direction L extends from the proximal end towards the distal end of the tip part assembly.

The camera assembly 6 includes a flexible printed circuit 70 and a camera module 60. The camera module 60 includes a camera module housing, in which an image sensor (not shown) and a lens stack (not shown) is housed, and extends in the longitudinal direction L. The camera module 60 comprises a proximal connection surface 60a. The tip part assembly comprises one single camera module 60.

Flexible printed circuits (FPCs) or flex prints are well-known electronic items that can be manufactured by technologies such as flexible electronics or flex circuits. The FPC may, throughout this specification, be a single- or double-sided flexible circuit or a rigid-flex circuit and may comprise one or more layers of conductive material and two or more layers of insulating material, and/or may be a flexible flat cable having one or more conductors. It should be understood that the term "printed" is used generically to denote placement of copper layers or tracings on a substrate and does not limit a PCB to the particular method of placing the copper layers or tracings on the board. Therefore a flexible printed circuit can be described, generically, as a flexible circuit or a flexible circuit board. The flexible circuit can comprise flat cables arranged at various angles, as described below.

Figure 9:
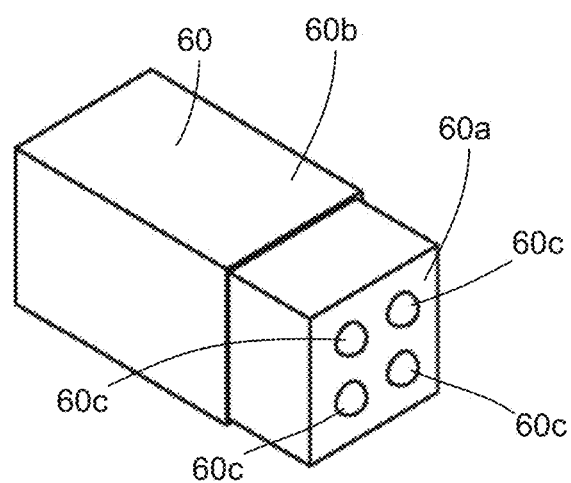
FIG. 9 is a perspective view of an embodiment of a camera assembly showing connection points.

The camera module 60 is positioned above the working channel 7 (best seen in FIGS. 4a and 4b) in a top-down direction TD so that a lateral direction T extends laterally from both the camera module 60 and the working channel 7, The connection surface 60a of the camera module comprises connection points 60c (an example is shown in FIG. 9) in electrical connection with the FPC 70. The FPC 70 comprises at a first portion 70a overlapping the connection surface 60a and comprising connection points (not shown) electrically connected with the connection points of the connection surface 60a of the camera module 60.

The flexible printed circuit 70 continues from the first portion 70a in the lateral or transverse direction T into a first fold 70b of the flexible printed circuit 70 which is curved towards the proximal end of the tip part assembly. The first fold 70b is arranged proximally of the camera module connection surface 60a. The first fold 70b extends into a third fold 70d, which extends into a second portion 70f of the FPC. Thusly the first fold and the third fold, which have centers of curvature on opposite sides of the FPC, connect the first portion and the second portion.

The first fold 70b is the first fold which the flexible printed circuit 70 extends into when continuing in the lateral direction T beyond the camera module connection surface 60a.

The first fold 70b is arranged proximally of the camera module connection surface 60a in the longitudinal direction L. As shown e.g. in FIG. 3c, the entire first fold 70b is arranged proximally of the camera module connection surface 60a.

Figures 3A, 3B:
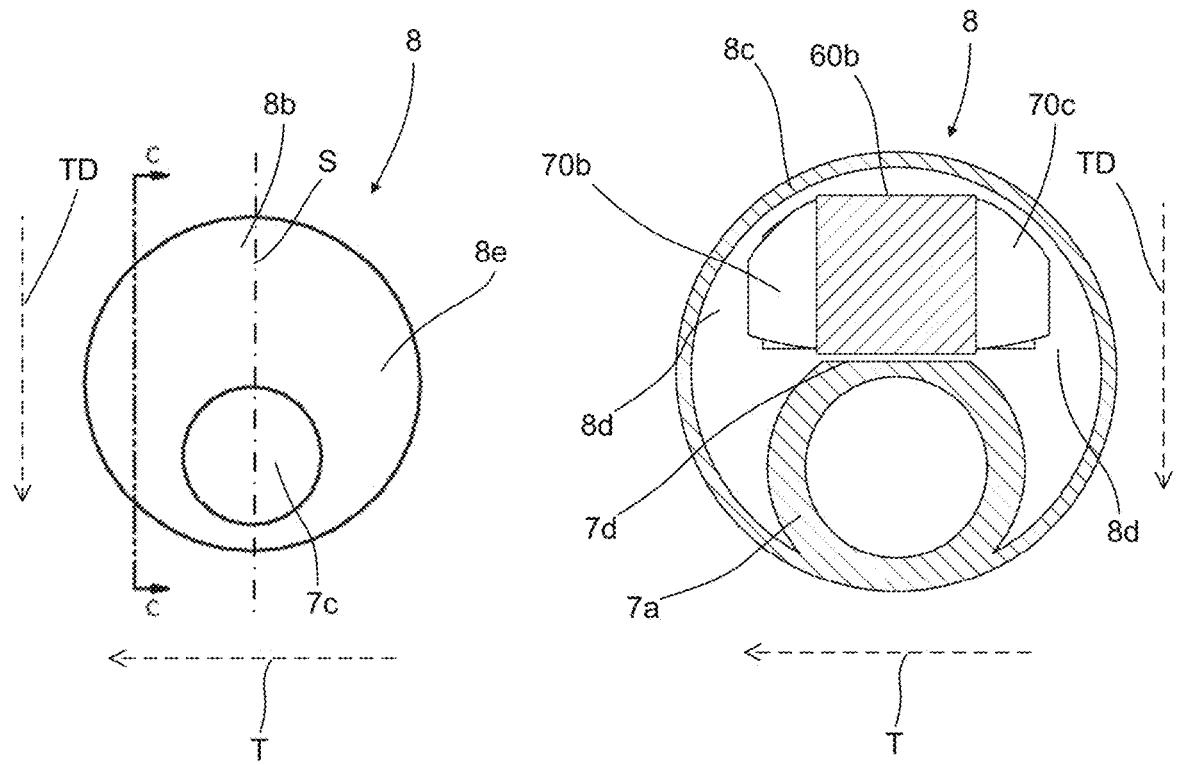

As seen in e.g. FIGS. 2b and 3b, the FPC 70 does not comprise any folds in the top-down direction TD. The FPC 70 is arranged so that no part of the FPC 70 is arranged above or below the camera module 60 in the top-down direction TD. The FPC 70 is furthermore arranged so that no part of the FPC 70 is arranged laterally of the camera module 60 distally of connection surface 60a, e.g. adjacent to the camera module 60 in a lateral direction T.

The flexible printed circuit 70 from the first portion 70a also extends in an opposite lateral direction beyond the connection surface into a second fold 70c towards the proximal end 8a of the housing 8. The opposite lateral direction extends substantially oppositely to the lateral direction T. The second fold 70c extends into a fourth fold 70e of the FPC 70 which extends into a third portion 70f of the FPC 70. Thusly the second fold and the fourth fold, which have centers of curvature on opposite sides of the FPC, connect the first portion and the third portion.

The connection surface 60a of the camera module 60 lies in a connection surface plane. The first fold 70b of the FPC 70 is arranged proximally of the connection surface plane.

The flexible printed circuit 70 continues from the connection to the connection surface 60a and continues towards the proximal end into the first fold 70b towards the proximal end of the tip part assembly. The flexible printed circuit 70 furthermore continues towards the proximal end. The flexible printed circuit 70 continues away from the connection surface plane 60a.

The FPC 70 is a single-sided flexible circuit comprising one layer of conductive material and two layers of insulating material.

The distal end of the tip part assembly may form a distal end 3b of the endoscope 1.

The housing 8 has a circumferentially extending outer surface 8c for facing the environment. The outer surface 8c encloses a volume and extends in the longitudinal direction L between a proximal end 8a and a distal end 8b of the housing 8. The first portion 7a of the working channel 7 is housed in the housing 8 and comprises an opening 7c in a distal surface 8e of the housing 8. The camera assembly 6 also housed in the housing 8.

The lateral volume 8d of the housing 8 is used for proximally directed first fold 70b, second fold 70c, third fold 70d, and fourth fold 70e of the FCP 70. This volume is located laterally of or at a side of the camera module 60 and of the working channel 7 positioned one above the other. So, the fold of the FPC is located in the volume 8d of the housing 8 at the lateral side of the camera module and FPC 70 where there is typically more room. Therefore, the outer diameter or the cross-sectional extent of the housing and thus the tip part assembly can be reduced. The outer diameter of the housing 8 is here 2.9 mm.

Figure 3C:
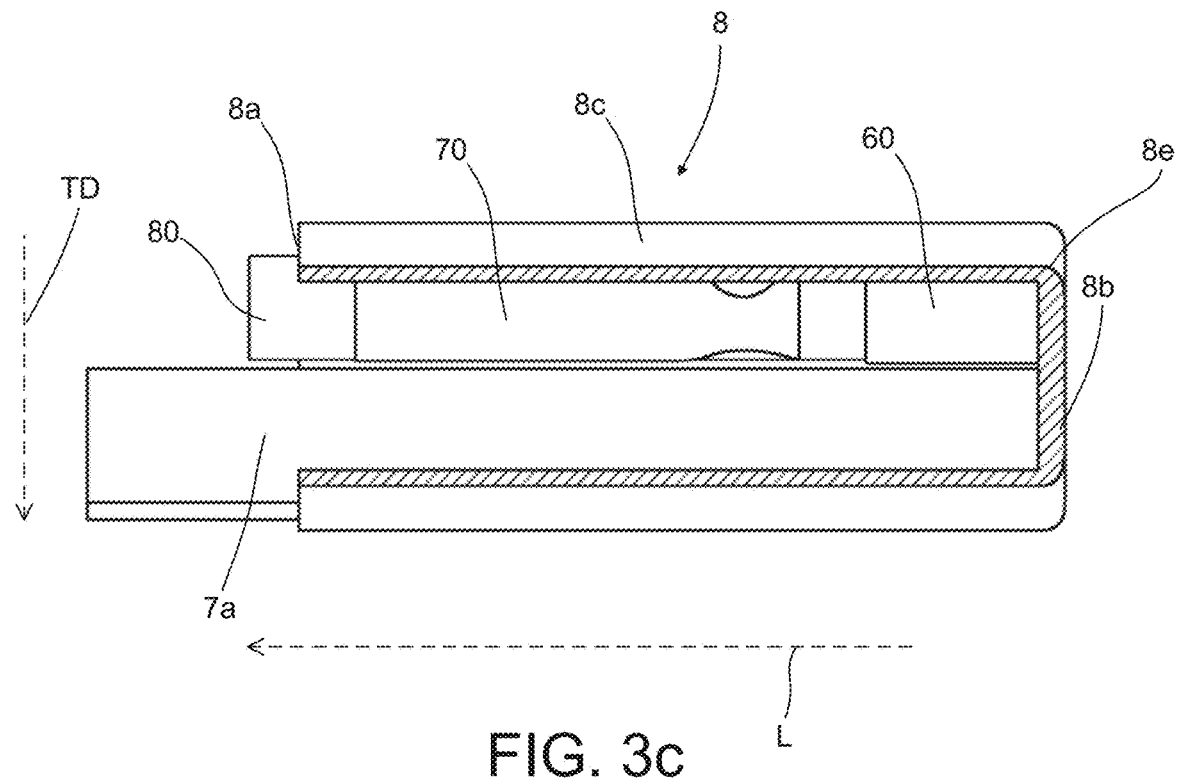

The first fold 70b, second fold 70c, third fold 70d and fourth fold 70e of the flexible printed circuit 70 are arranged proximally of the camera module connection surface 60a, as e.g. seen in FIG. 3c.

The first fold 70b as well as the second fold 70c of the flexible printed circuit 70 are arranged adjacent to an inner lateral surface of a circumferential wall of the housing 8. "Adjacent" may in this text be immediately adjacent. As shown e.g. in FIGS. 2a-2b and 3b-3c, no part of the tip part is positioned between the first fold 70b and the housing 8, nor between the second fold 70c and the housing. The folds 70a-70d of the FPC are positioned immediately adjacent to the tip part housing 8 and with no part of the tip part assembly being positioned in between the FPC folds 70a-70d and the circumferential wall of the housing 8. The first fold 70b is positioned close to the circumferential wall, at a distance smaller than a circumscribed circle of a cross-section of both the circumferential wall and the first fold 70b.

A plane of symmetry S passes through a longitudinally extending centre line (shown in FIG. 3a) of the working channel 7, extending from a proximal end towards the distal end of the working channel 7, and through a longitudinally extending centre line (not shown) of the camera module 60, parallel to the centre line of the of the camera module. The FPC 70 extends from the first portion 70a perpendicularly to the plane of symmetry S.

The second fold 70c, fourth fold 70e and third portion 70f are provided in a similar manner mirrored about symmetry plane S to the first fold 70b, third fold 70d and second portion 70f, respectively.

The first 70b and second folds 70c continue to be connected in the first portion 70a of the FPC 70.

Referring now to FIGS. 3a-3c, the working channel 7 has a first portion 7a with a circumferentially extending circular cylindrical outer wall enclosing a working channel spacing. The working channel 7 has an inner diameter of 1.2 mm. A wall thickness of a circumferential wall of the first portion 7a of the working channel 7 is 0.2 mm. An opening 7c of the working channel 7 has a diameter of 1 mm.

The first portion 7a of the working channel 7 has a chamfered portion 7d, which faces the camera module 60. The chamfered portion 7d is positioned with a distance to the camera assembly 6. The chamfered portion 7d reduces the wall thickness of the first portion 7a to reduce the cross-section of the tip of the endoscope.

The chamfered portion 7d is formed in one piece with the circumferential wall of the working channel first portion 7a. The wall thickness of the chamfered portion of the circumferential wall is smaller at the portion facing the camera module 60 than along at least one other portion of the circumferential wall of the working channel first portion 7a.

The working channel 7 allows liquid to be removed from a body cavity or allows insertion of surgical instruments or the like into the body cavity. The working channel 7 extends from a proximal end of an endoscope to a distal end of the endoscope 1.

The camera module 60 and the working channel 7 are positioned bottom-to-top. A top surface 60b of the camera module 60 is be positioned adjacent to an inner top surface of a circumferential wall 8c of the housing 8 of the tip part assembly 5. The first fold 70b of the FPC 70 is positioned adjacent to an inner lateral surface of the circumferential wall 8c of the housing 8. A folding radius of the first fold 70b (and/or the second fold 70c and/or the third fold 70d and/or fourth fold 70e), as mentioned below) is in 0.4 mm.

A maximum extent in the longitudinal direction L from the distal end of the tip part assembly 5 to a proximal end 8b of the housing 8 or FPC is 10 mm.

The longitudinal direction L extends at a right angle to the top-down TD and lateral T directions, and the top-down TP and lateral T directions extends at a right angle to each other.

An electrical component 71 is arranged on the second portion 70f of the FPC 70. In some embodiments, electrical components extend on both sides of the symmetry plane S, e.g. on the third portion 70f. The electrical component 71 is here a capacitor.

The first fold 70b is folded with a 135-degree folding angle.

The working channel 7 further comprises a second portion 7b. The second portion is connected liquid tight to the first portion 7a by an adhesive. The working channel second portion 7b extends along the proximal-distal direction PD through the insertion tube 3 to the proximal end 3a of the insertion tube 3. The second portion 7b is provided as a flexible tube.

The housing 8 is molded in one piece, and the housing outer surface 8c and the housing end wall 8e is thus provided in one piece. The housing 8 is made from a transparent material. The housing 8 is an exterior housing.

The housing 8 comprises a tubular wall with an outer surface 8c and enclosing a volume, i.e. a spacing within the housing 8. This spacing is also defined by a distal end wall 8e of the housing 8. An opening 7c for the working channel 7 is provided in the end wall 8e. The opening is provided by the one-piece molding of the housing 8 with the first portion 7a of the working channel 7.

A lateral portion 8d of the volume of the housing 8 is defined laterally from the camera module 60 and the working channel 7, the lateral volume 8d extending between the proximal end 8a and the distal end 8b of the housing 8.

The housing 8 is an exterior housing which is exterior with respect to the camera assembly 6, the working channel first portion 7a and the support 80 partly or entirely housed therein.

The circumferential wall has a longitudinal centre axis extending between a distal end 8b and a proximal end 8a of the housing 8. The working channel first portion 7a has a longitudinal centre axis extending in parallel with a centre axis of the housing 8, and the camera module 60 has a longitudinal centre axis extending in parallel with the longitudinal centre axis of the housing 8. The first fold 70b of the FPC is be folded about a folding axis A lying in a plane in parallel with this centre plane. The centre plane here lies in the symmetry plane S. Second fold 70c, third fold 70d, and fourth fold 70e have similar folding axes.

The tip part assembly 5 further comprises a support 80 for the flexible printed circuit 70, and the first fold 70b is folded about a first folding portion, or first lobe, 80b of the support 80. The support 80 is a support bracket.

The support 80 is T-shaped when seen in the top-down direction TP and comprises a main portion 80a having a first lateral surface LS1 laying on a plane LP1, and a second lateral surface LS2 opposite the first lateral surface LS1, the first folding portion 80b and a second folding portion 80c. The two folding portions 80b and 80c are each rounded when seen in the top-down direction TD. The two folding portions 80b and 80c are provided as the upper part of the T-shape of the support 80. The upper part 80b, 80c of the T-shaped support 80 extends in the lateral direction T, and the main portion 80a extends in the longitudinal direction L. The support main portion 80a extends at a right angle to the folding portions 80b, 80c.

The support 80 extends in the longitudinal direction L. The shape of the first folding portion 80b of the support 80 corresponds to the first fold 70b of the FPC 70. The first folding portion 80b of the support 80 comprises two rounded sections, and the rounded sections each have a rounding radius corresponding to the folding radius of the first 70b and third folds 70d of the FPC 70.

The same support is used for both the first fold 70b and the second fold 70c as well as the third fold 70d and the fourth fold 70e. The second fold 70c and the fourth fold 70e are folded about the second folding portion 80c of the support. A rounding radius of the two folding portions 80b, 80c correspond to a respective folding radius of the first fold 70b and the third fold 70d and the second fold 70c and the fourth fold 70e, respectively, arranged along a respective one of the folding portions 80b, 80c. The FPC 70 follows an outer contour of the support 80.

The FPC 70 is attached to a surface of the support 80 to extend along the support 80. The attachment is provided by means of a non-conducting adhesive.

Figure 4A:
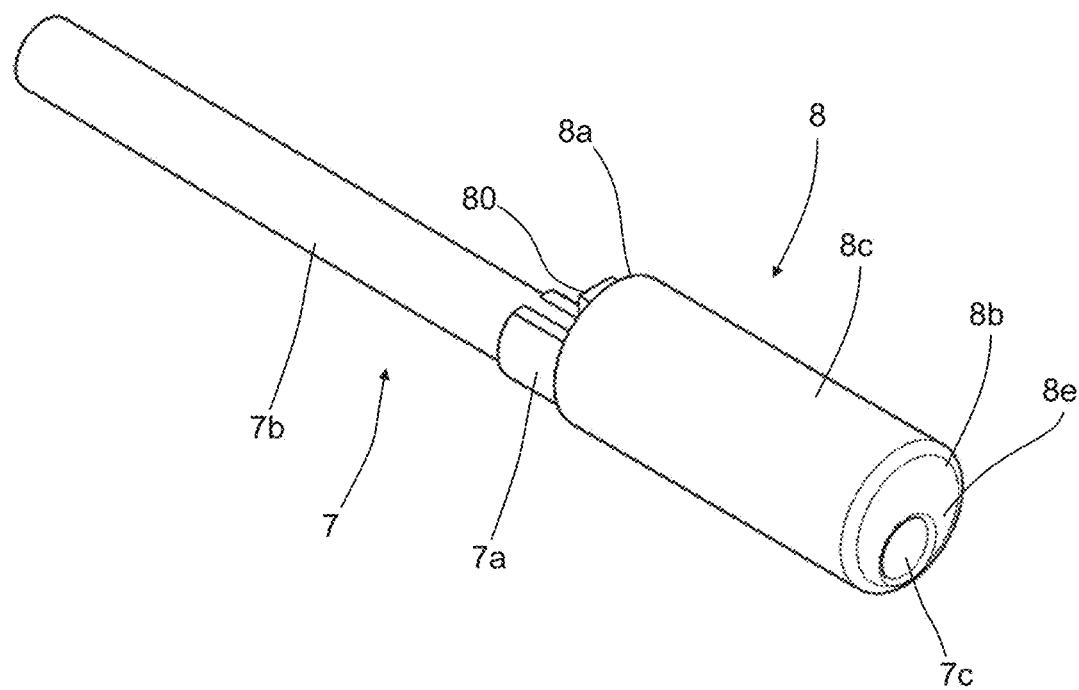
FIG. 4a shows a perspective view of the tip part assembly of FIG. 1a, FIG. 4b shows a perspective view of another embodiment of a tip part assembly.
Figure 4B:
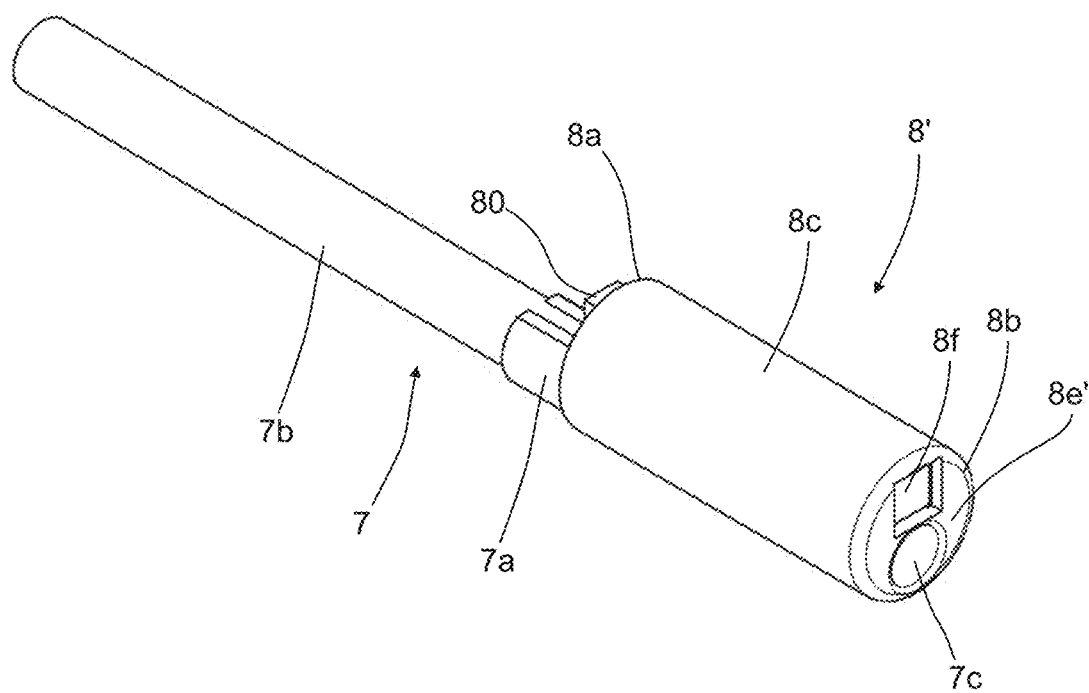

FIG. 4b shows a perspective view of a second, alternative embodiment of a tip part assembly according to the present disclosure. This second embodiment of the tip part assembly comprises the working channel 7 and additional components similar to the embodiment of the tip part assembly shown in FIGS. 1a-1b, 2a-2b, 3a-3c, and 4a.

A housing 8' comprises a proximal end 8a, a distal end 8b, and an outer surface 8c similar to the housing 8 described above. The housing 8' moreover comprises an end wall 8e' having an opening, i.e. a window 8f, arranged distally of the camera module. The window 8f is arranged such that access is provided to a distal end of the camera module is provided. The window 8f thereby has the same area and dimensions in the lateral T and up-down directions UD as the distalmost part of the camera module.

Adhesive is provided around the opening 8f, providing a liquid sealing of the camera module towards the exterior of the housing 8'.

Figure 5A:
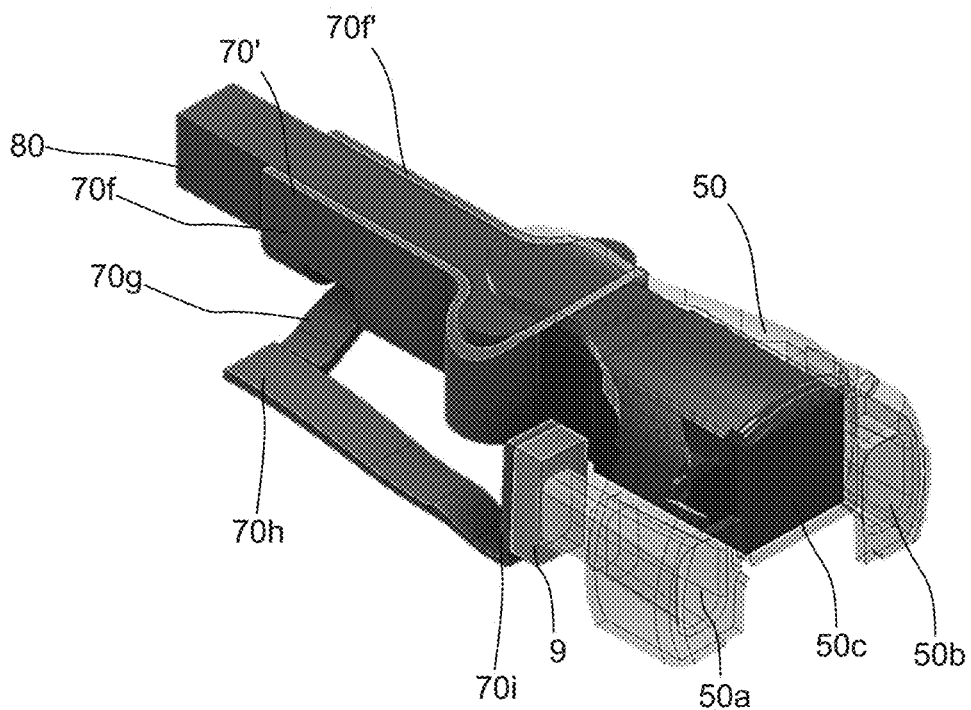
FIG. 5a shows a perspective view of an embodiment of a camera assembly and a support of a tip part assembly.

FIG. 5a shows a second embodiment of a camera assembly 6' to be used in a tip part assembly according to the present disclosure. The second camera assembly 6' comprises a camera module 60 and a support 80 similar to the first embodiment of the camera assembly 6 described above.

An FPC 70' comprises portions 70a-70f and 70f similar to the FPC 70 described above. The FPC 70' further comprises a first LED portion, or fourth portion, 70g, a second LED portion, or fifth portion, 70h and a third LED portion, or light emitting diode portion, 70i leading to and establishing an electrical connection with an LED 9 of the tip part assembly. The first LED portion 70g of the FPC 70' extends from and is connected to and formed in one piece with the third portion 70f, of the FPC 70'.

The first LED portion 70g extends below the support 80 when seen in the top-down direction (not shown) and continues to the second LED portion 70h and into the third LED portion 70i, which is electrically connected to the LED 9. The first 70g, second 70h and third LED portions 70i each comprise one fold providing a connection to the FPC second portion 70', the first LED portion 70g, and the second LED portion 70h, respectively.

The third LED portion 70i is electrically connected to the LED 9 by anisotropic conductive film (ACF) bonding.

The LED 9 abuts a light guide part 50 to be arranged at the distal end of the tip part assembly and has a connection surface (not shown) extending in parallel to the connection surface 60a of the camera module 60. The third LED portion 70i of the FPC 70' extends in parallel with the connection surface of the LED 9. The LED 9 is arranged beside the camera module 60 in the lateral direction T.

The first 70g, second 70h and third LED portions 70i are connected to and formed in one piece with each other as well as the third portion 70f' of the FPC 70f'.

The camera assembly 6' further comprises a second LED (not shown) and corresponding first, second, and third LED portions (not shown) of the FPC 70'. These are provided symmetrically around a symmetry plane (not shown) provided similarly to the symmetry plane S of the camera assembly 6.

Figure 5B:
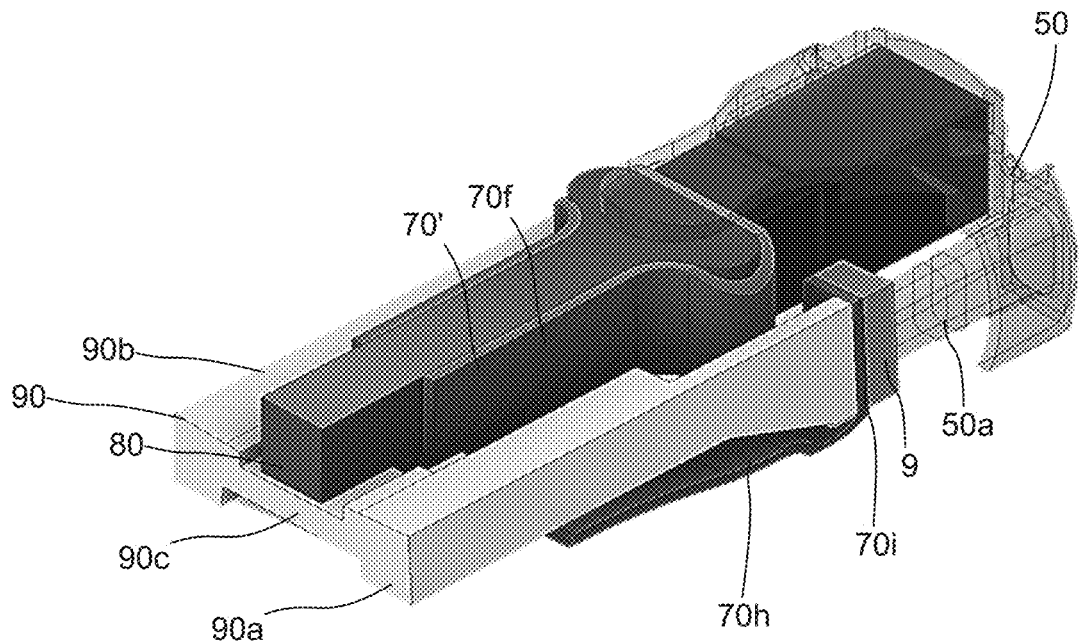
FIG. 5b shows another perspective view of the embodiment of the camera assembly and support of FIG. 5a with an LED holder.

FIG. 5b shows the camera assembly 6' of FIG. 5a further comprising an LED holder 90. The LED holder 90 comprises a first portion 90a extending in the longitudinal direction L. The LED holder first portion 90a abuts the third LED portion 70i of the FPC 70' so as to support the third LED portion 70i and/or the LED 9. The LED holder 90 comprises a second portion 90b, which abuts and support the third LED portion 70i of the FPC 70 and thereby the LED 9. The LED holder first 90a and second portions 90b are interconnected by an interconnecting portion 90c of the LED holder 90. The interconnecting portion 90c is proximally, i.e. further towards the proximal end of the tip part assembly, of the first LED portion 70g of the FPC 70'. The LED holder 90 is made from crylonitrile butadiene styrene (ABS) and is manufactured by means of molding. The LED holder 90 is manufactured in one piece.

The light guide part 50 includes two light guides 50a, 50b for guiding light from respective LED 9 to e.g. a front or proximal end surface or end wall of the tip part assembly and/or a housing thereof. The light guide part 50 further comprises a camera lens cover portion 50c, arranged distally of and abutting the distal end of the camera module 60.

The light guides 50a, 50b are molded in one piece with the lens cover portion. The light guide 50a, 50b extends from a distal end of the tip part assembly to a respective LED 9. The light guide part and thus the light guides 50a, 50b are made from a transparent material.

The LEDs 9 may comprise a light emitting surface. The light emitting surface(s) may emit light in the proximal-distal direction. The light emitting surface(s) may be positioned in abutment with a housing, where this is provided, or in abutment with one or more light guides.

Figure 6:
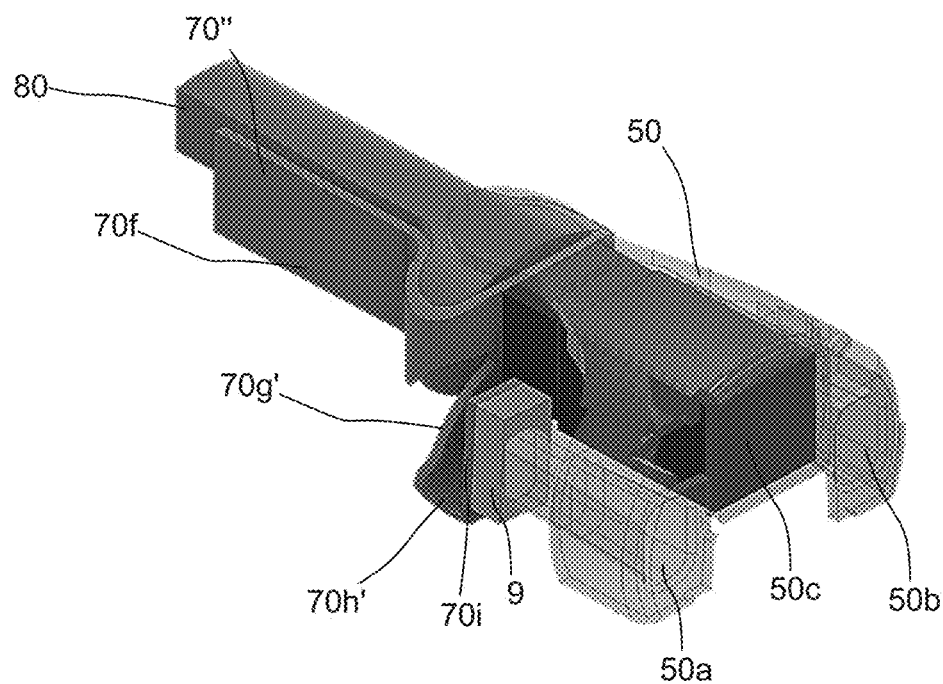
FIG. 6 shows a perspective view of yet another embodiment of a camera assembly and support of a distal tip assembly.

FIG. 6 shows a third embodiment of a camera assembly 6" to be used in a tip part assembly according to the present disclosure. The third camera assembly 6" comprises a camera module 60 and a support 80 similar to the first 6 and second embodiment of the camera assembly 6' described above.

The FPC 70" comprises portions 70a-70f and 70f' similar to the FPC 70 described above.

The FPC 70" comprises a first LED portion 70g', which extends from, is connected to, and is formed in one piece with the first portion 70a of the FPC 70", which is connected to the connection surface 60a of the camera module 60. The FPC 70" further comprises a second 70h' and a third LED 70i portions. The third LED portion 70i is electrically connected to the LED 9 and the second LED portion 70h', with which the third LED portion 70i is also formed in one piece. The second LED portion 70h' is further electrically connected to and formed in one piece with the first LED portion 70g'. Similar to the second embodiment of the camera assembly, the LED portions 70g', 70h' and 70i further comprise folds.

The first LED portion 70g', second LED portion 70h' and third LED portion 70i are connected to and formed in one piece with each other as well as the second portion 70f of the FPC 70", which is connected to the connection surface 60a of the camera module 60.

Figure 7:
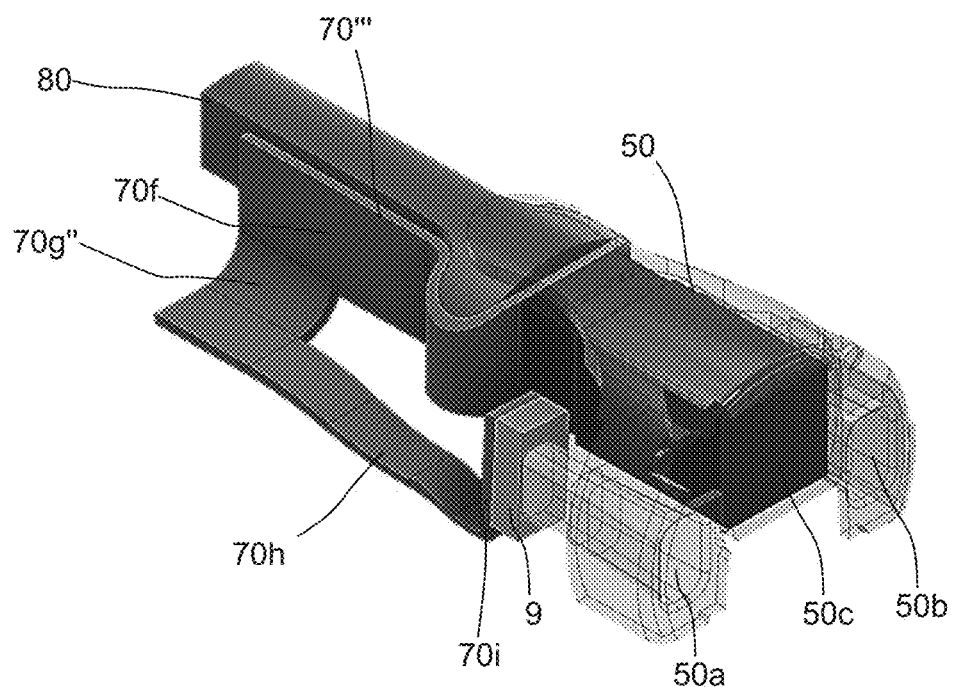
FIG. 7 shows a perspective view of a further embodiment of a camera assembly and support of a distal tip assembly.

FIG. 7 shows a fourth embodiment of a camera assembly 6''' to be used in a tip part assembly according to the present disclosure. The third camera assembly 6''' comprises a camera module 60 and a support 80 similar to the first 6 and second embodiment of the camera assembly 6' described above.

An FPC 70''' comprises portions 70a-70f, 70f, 70h, 70i similar to the FPCs 70, 70', 70" described above. The first LED portion, or fourth portion, 70g" of the FPC 70''' is here connected to and formed in one piece with the second portion 70f and thereby remains on the same side of the support 80. The second LED portion, or fifth portion, 70h, described above, extends distally from the fourth portion 70g".

Properties of the various portions 70a-f, 70f, 70g, 70g', 70g", 70h, 70h', and 70i may be the same for the various embodiments shown in FIGS. 5a, 5b, 6, and 7.

Turning to FIG. 8, a bending section 4 is provided. The bending section 4 comprises a number of hingedly connected segments including a distal end segment 41, a proximal end segment 43, and a plurality of intermediate segments 42 positioned between the distal end segment 41 and the proximal end segment 43. The distal end segment 41 is adapted for being connected and/or attached to a housing of a tip part assembly, such as the housing 8 of FIGS. 3a-3c and 4a or the housing 8' of FIG. 4b, at a proximal end of the housing.

The following embodiments expand and further exemplify the features described above:

1. A tip part assembly for an endoscope, the tip part assembly having a proximal end for being connected to other parts of the endoscope and a distal end positioned oppositely from the proximal end for forming a distal end of the endoscope, the tip part assembly comprising:
    a working channel extending in a longitudinal direction, the longitudinal direction extending from the proximal end towards the distal end of the tip part assembly, and
    a camera assembly including a flexible printed circuit and a camera module, the camera module including an image sensor and a lens stack and extending in the longitudinal direction, the camera module comprising a proximal connection surface,
    wherein the camera module is positioned above the working channel in a top-down direction so that a lateral direction extends laterally from both the camera module and the working channel,
    wherein the flexible printed circuit from a connection to the connection surface of the camera module continues in the lateral direction beyond the connection surface into a first fold of the flexible printed circuit towards the proximal end of the tip part assembly.

2. A tip part assembly according to embodiment 1, wherein the longitudinal direction extends at a substantially right angle to the top-down and lateral directions, and the top-down and lateral directions extend at a substantially right angle to each other.

3. A tip part assembly according to embodiment 1 or 2, wherein a plane of symmetry passes through a longitudinally extending centre line of the working channel and through a longitudinally extending centre line of the camera module, wherein the flexible printed circuit from the connection to the connection surface of the camera module extends approximately perpendicular to the plane of symmetry.

4. A tip part assembly according to any one of the previous embodiments, wherein the first fold bends or folds with an angle from 90 to 180 degrees.

5. A tip part assembly according to any one of the previous embodiments, wherein the tip part assembly includes a housing having a circumferentially extending outer surface for facing the environment, the outer surface enclosing a volume and extending in a longitudinal direction between a proximal end and a distal end of the housing, the working channel being at least partly housed in the housing and comprising an opening in a distal surface of the housing, the camera assembly being at least partly housed in the housing.

6. A tip part assembly according to embodiment 5, wherein the circumferential wall has a longitudinal centre axis extending between a distal end and a proximal end of the housing, the working channel has a longitudinal centre axis extending in parallel with a centre axis of the housing, and the camera module has a longitudinal centre axis extending substantially in parallel to the longitudinal centre axis of the housing, and wherein a centre plane of the tip part assembly substantially coincides with the longitudinal centre axis of the camera module and the longitudinal centre axis of the working channel, the fold of the FPC being folded about a folding axis lying in a plane substantially parallel with this centre plane.

7. A tip part assembly according to embodiment 5 or 6, wherein a lateral portion of the volume of the housing is defined laterally from the camera module and the working channel, the lateral volume extending between the proximal end and the distal end of the housing, an FPC first portion or connections thereof being electrically connected to the at least one connection of the connection surface, the first portion being positioned face-to-face with the connection surface and extending into a second portion of the FPC, the second portion extending laterally from the first portion beyond the connection surface and into the lateral spacing portion, the second portion comprising the first fold, the first fold being positioned in the lateral spacing portion.

8. A tip part assembly according to any one of the previous embodiments, wherein the flexible printed circuit from the connection to the connection surface of the camera module also extends in an opposite lateral direction beyond the connection surface into a second fold of the flexible printed circuit towards the proximal end of the housing, the opposite lateral direction extending substantially oppositely to the lateral direction.

9. A tip part assembly according to any one of the previous embodiments, further comprising a support for the flexible printed circuit, the first fold being folded about a folding portion of the support.

10. A tip part assembly according to any one of the previous embodiments, wherein the FPC continues or extends further from the first fold into a third fold of the flexible circuit board, the third fold folding in a direction opposite to the first bend.

11. A tip part assembly according to any one of the previous embodiments, wherein the lens stack is positioned proximally of or in front of the image sensor and includes two or more lenses including a proximal lens and a distal lens, the camera module further comprising a lens barrel which holds the lens stack, the lens stack being stacked in the longitudinal direction, the lens barrel extending in the longitudinal direction.

12. A tip part assembly according to any one of the previous embodiments, wherein the third fold bends or folds with an angle from 0 to 90 degrees.

13. A tip part assembly according to any one of the previous embodiments, wherein an outer maximum extent in the lateral direction of the tip part assembly is less than 3.3 mm.

14. A tip part assembly according to any one of the previous embodiments, further comprising a bending section having a distal end segment connected to a housing of the tip part assembly.

15. A method for assembly of a tip part assembly for an endoscope, the tip part assembly having a proximal end for being connected to other parts of the endoscope and a distal end positioned oppositely from the proximal end for forming a distal end of the endoscope, the method comprising the steps of:
   a) providing a working channel of the tip part assembly, the working channel extending in the longitudinal direction,
   b) providing a camera assembly of the tip part assembly, the camera assembly including a flexible circuit board and a camera module, the camera module including an image sensor and a lens stack and extending in the longitudinal direction, the camera module comprising a proximal connection surface,
   c) positioning the camera module above the working channel in a top-down direction so that a lateral direction extends laterally from both the camera module and the working channel,
   d) connecting the flexible printed circuit to the connection surface of the camera module so that the flexible printed circuit continues in the lateral direction beyond the connection surface, and
   e) folding a first fold towards the proximal end of the tip part assembly in that part of the flexible printed circuit that continues in the lateral direction beyond the connection surface.

16. A method according to embodiment 15, comprising the further steps of:
   f) providing a housing of the tip part assembly, the housing having a circumferentially extending outer surface for facing the environment, the outer surface enclosing a volume and extending in a longitudinal direction between a proximal end and a distal end of the housing,
   g) positioning the working channel at least partly in the housing so that the working channel comprises an opening in a distal surface of the housing,
   h) positioning the camera assembly at least partly in the housing.

17. A method according to embodiment 15 or 16, wherein, in step e), the first fold is folded about a folding part of a support of the tip part assembly.

18. An endoscope comprising a tip part assembly according to any one of embodiments 1 to 14 or a tip part assembly manufactured according to any one of embodiments 15 to 17.

LIST OF REFERENCES

The following is a list of reference numerals used throughout this specification.

1 endoscope
11 monitor
12 cable socket
13 monitor cable
2 handle
21 control lever
3 insertion tube 3a proximal end
3b distal end
4 bending section
41 distal end segment
42 intermediate segment
43 proximal end segment
5 tip part
5 light guide part
50a first light guide
50b second light guide
50c lens cover portion
6 camera assembly
6' camera assembly
6" camera assembly
6''' camera assembly
60 camera module
60a camera module connection surface
60b camera module top surface
7 working channel
7a first working channel portion
7b second working channel portion
7c working channel distal opening
7d working channel chamfered portion
70 flexible printed circuit (FPC)
70' flexible printed circuit (FPC)
70" flexible printed circuit (FPC)
70''' flexible printed circuit (FPC)
70a FPC first portion
70b FPC first fold
70c FPC second fold
70d FPC third fold
70e FPC fourth fold
70f FPC second portion
70f' FPC second portion
70g first LED portion
70g' first LED portion
70g" first LED portion
70h second LED portion
70h' second LED portion
70i third LED portion
71 electrical component
8 housing
8' housing
8a housing proximal end
8b housing distal end
8c outer surface
8d lateral spacing portion
8e housing end wall
8e' housing end wall
8f window
80 support
80a support main portion
80b first folding portion
80c second folding portion
9 light-emitting diode (LED)
90 LED holder
90a LED holder first portion
90b LED holder second portion
90c LED holder interconnection portion
A folding axis
L longitudinal direction
PD proximal-distal direction
S symmetry plane
TD top-down direction

The invention claimed is:

1. An endoscope comprising:
a tip assembly having a proximal end opposite a distal end and including:
a working channel extending in a longitudinal direction, the longitudinal direction extending from the proximal end toward the distal end;
a camera assembly including a flexible printed circuit and a camera module, the camera module having an image sensor and a lens and extending in the longitudinal direction, the camera module positioned above the working channel in a top-down direction and having a proximal connection surface; and
a flexible printed circuit support having a proximal end, a distal end, and a symmetry plane passing through the camera module and a longitudinally extending center line of the working channel, the proximal end comprising a longitudinal portion having a first lateral surface laying on a plane, the distal end including a first lobe extending laterally relative to the symmetry plane further than the camera module and the plane on which the first lateral surface lies,
wherein the flexible printed circuit comprises a first portion overlapping the proximal connection surface, a second portion, and a first fold extending laterally, relative to the top-down direction, from the first portion and toward the proximal end, and
wherein the first fold curves about the first lobe.

2. The endoscope of claim 1, wherein the flexible printed circuit comprises a second portion extending proximally from the first fold.

3. The endoscope of claim 2, wherein the longitudinal portion of the flexible printed circuit support comprises the first lateral surface and a second lateral surface, and wherein the second portion abuts the first lateral surface of the longitudinal portion.

4. The endoscope of claim 3, wherein the flexible printed circuit support comprises a distal surface perpendicular to the symmetry plane and abutting the first portion of the flexible printed circuit.

5. The endoscope of claim 3, wherein the flexible printed circuit comprises a second fold and a third fold connecting the first fold and the second portion, the second fold abutting the flexible printed circuit support.

6. The endoscope of claim 5, wherein the first fold has a first folding axis and the second fold has a second folding axis, the first folding axis being parallel with the second folding axis, and wherein the first folding axis and the second folding axis are on opposite sides of a portion of the flexible circuit board.

7. The endoscope of claim 3, wherein the flexible printed circuit support comprises a second lobe extending laterally relative to the symmetry plane and opposite the first lobe, wherein the flexible printed circuit comprises a second fold extending from the first portion and a third portion extending from the second fold, wherein the second fold curves about the second lobe and the third portion abuts the second lateral surface of the longitudinal portion.

8. The endoscope of claim 7, wherein the flexible printed circuit comprises a fourth portion extending laterally from the second portion or the third portion, a fifth portion extending distally from the fourth portion, and a light emitting diode portion extending from the fifth portion in the top-down direction, wherein the endoscope further comprises a light emitting diode electrically connected to the light emitting diode portion.

9. The endoscope of claim 8, further comprising a light guide adjacent the light emitting diode and positioned proximally thereof.

10. The endoscope of claim 9, further comprising a light emitting diode holder comprising a proximal portion and a first portion extending distally from the proximal portion and having a distal surface abutting the light emitting diode portion of the flexible circuit board.

11. The endoscope of claim 2, wherein the endoscope includes a housing enclosing a volume and having a circumferentially extending outer surface extending in the longitudinal direction, the working channel being at least partly housed in the housing and comprising an opening in a distal surface of the housing, the camera assembly being at least partly housed in the housing.

12. The endoscope of claim 11, wherein the working channel has a longitudinal centre axis, and wherein the first fold curves about a folding axis that is substantially perpendicular to the longitudinal centre axis.

13. The endoscope of claim 12, further comprising a bending section having a distal end segment connected to the housing.

14. A method to manufacture a tip assembly of an endoscope, the method comprising:
providing a camera module having an image sensor and a lens and extending in the longitudinal direction, the camera module having a proximal connection surface;
connecting a first portion of a flexible printed circuit to the connection surface of the camera module, the flexible printed circuit extending in a lateral direction, relative to a top-down direction, beyond the first portion;
providing a flexible printed circuit support having a proximal end, a distal end, and a symmetry plane passing through the camera module and a longitudinally extending center line of the working channel, the proximal end comprising a longitudinal portion having a lateral surface laying on a plane, the distal end including a first lobe extending laterally relative to the symmetry plane further than the camera module and the plane on which the lateral surface lies,
folding a portion of the flexible printed circuit that extends in the lateral direction into a first fold about the first lobe, wherein the first fold is arranged proximally of the camera module connection surface; and
positioning the camera module above the working channel to define the top-down direction.

15. The method of claim 14, further comprising providing a housing having a volume therein and a circumferentially extending outer surface, wherein positioning the camera module above a working channel includes inserting the camera assembly at least partly in the housing from a proximal end of the housing.

16. The method of claim 15,
wherein the longitudinal portion of the flexible printed circuit support comprises lateral surfaces and the distal end further comprises a second lobe extending laterally opposite the first lobe, the method further comprising:
abutting a distal surface of the distal end of the flexible printed circuit support onto the first portion of the flexible circuit board, and
folding another portion of the flexible printed circuit that extends in the lateral direction into a second fold around the second lobe.

17. The method of claim 16, wherein the flexible circuit board includes a light emitting diode portion, the method further comprising:
connecting a light emitting diode to the light emitting diode portion of the flexible circuit board; and
providing a light emitting diode holder comprising a proximal portion and a first portion extending distally from the proximal portion and having a distal surface abutting the light emitting diode portion of the flexible circuit board.

18. The method of claim 16, further comprising forming a second fold of the flexible printed circuit about the second lobe, and abutting a third portion, extending from the second fold, to another of the lateral surfaces of the longitudinal portion.

19. The method of claim 18, wherein the flexible printed circuit comprises a fourth portion extending laterally from the second portion or the third portion, a fifth portion extending distally from the fourth portion, and a light emitting diode portion extending from the fifth portion in the top-down direction, the method further comprising electrically connecting a light emitting diode to the light emitting diode portion.

20. The method of claim 14, wherein the camera module, the flexible printed circuit, and the flexible printed circuit support form a camera assembly, further comprising providing a housing having a circumferential wall that extends longitudinally and has an internal diameter, and inserting the camera assembly at least partly into the housing, wherein the flexible printed circuit support comprises a second lobe extending laterally relative to the symmetry plane and opposite the first lobe, and wherein the first lobe and the second lobe comprise cross-sections with corners adjacent the circumferential wall that are rounded, wherein the housing is sized such that the camera assembly fits in the housing due to the rounder corners and the camera assembly would not fit in the housing if the corners were not rounded.

21. The endoscope of claim 1, wherein the tip assembly includes a housing having a circumferential wall that extends longitudinally and has an internal diameter, the camera assembly being at least partly housed in the housing, wherein the flexible printed circuit support comprises a second lobe extending laterally relative to the symmetry plane and opposite the first lobe, and wherein the first lobe and the second lobe comprise cross-sections with corners adjacent the circumferential wall that are rounded.

22. The endoscope of claim 21, wherein the internal diameter of the circumferential wall of the housing is closer to the camera assembly than an intersection of a top surface of the camera assembly and a lateral extreme edge of the second lobe.

23. The endoscope of claim 1, wherein the tip assembly includes a housing having a circumferential wall that extends longitudinally and has an internal diameter, the camera assembly being at least partly housed in the housing, wherein the flexible printed circuit support comprises a second lobe extending laterally relative to the symmetry plane and opposite the first lobe, wherein the internal diameter of the circumferential wall of the housing is closer to the camera assembly than an intersection of a top surface of the camera assembly and a lateral extreme edge of the second lobe.

* * * * *